United States Patent
Banet et al.

(10) Patent No.: US 10,335,044 B2
(45) Date of Patent: *Jul. 2, 2019

(54) BODY-WORN SYSTEM FOR MEASURING CONTINUOUS NON-INVASIVE BLOOD PRESSURE (CNIBP)

(71) Applicant: Sotera Wireless, Inc., San Diego, CA (US)

(72) Inventors: Matthew Banet, San Diego, CA (US); Marshal Dhillon, San Diego, CA (US); Devin McCombie, San Diego, CA (US)

(73) Assignee: SOTERA WIRELESS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/614,349

(22) Filed: Jun. 5, 2017

(65) Prior Publication Data
US 2018/0055389 A1 Mar. 1, 2018

Related U.S. Application Data

(63) Continuation of application No. 12/650,392, filed on Dec. 30, 2009, now Pat. No. 9,668,656, which is a
(Continued)

(51) Int. Cl.
*A61B 5/021* (2006.01)
*A61B 5/00* (2006.01)
(Continued)

(52) U.S. Cl.
CPC ........ *A61B 5/02125* (2013.01); *A61B 5/0022* (2013.01); *A61B 5/0225* (2013.01);
(Continued)

(58) Field of Classification Search
CPC ... A61B 5/721; A61B 5/1455; A61B 5/02416; A61B 5/02422; A61B 5/02427; A61B 5/02433
See application file for complete search history.

(56) References Cited

U.S. PATENT DOCUMENTS

| 9,668,656 B2 * | 6/2017 | Banet | A61B 5/02125 |
| 2004/0034294 A1 * | 2/2004 | Kimball | A61B 5/02125 600/323 |

(Continued)

FOREIGN PATENT DOCUMENTS

| CN | 101150989 A | 3/2008 |
| WO | 2004107963 A2 | 12/2004 |

OTHER PUBLICATIONS

Office Action issued by SIPO in Chinese Patent Application No. 2015107854924 dated Oct. 25, 2017—incl Engl lang transl (16 pages total).

(Continued)

*Primary Examiner* — Meredith Weare
(74) *Attorney, Agent, or Firm* — Acuity Law Group, PC; Michael A. Whittaker

(57) ABSTRACT

The present invention provides a technique for continuous measurement of blood pressure based on pulse transit time and which does not require any external calibration. This technique, referred to herein as the 'Composite Method', is carried out with a body-worn monitor that measures blood pressure and other vital signs, and wirelessly transmits them to a remote monitor. A network of body-worn sensors, typically placed on the patient's right arm and chest, connect to the body-worn monitor and measure time-dependent ECG, PPG, accelerometer, and pressure waveforms. The disposable sensors can include a cuff that features an inflatable bladder coupled to a pressure sensor, three or more electrical sensors (e.g. electrodes), three or more accelerometers, a temperature sensor, and an optical sensor (e.g., a light source and photodiode) attached to the patient's thumb.

17 Claims, 27 Drawing Sheets

Fig. 27

Related U.S. Application Data continuation-in-part of application No. 12/138,194, filed on Jun. 12, 2008, now Pat. No. 8,419,649.

(60) Provisional application No. 60/983,198, filed on Oct. 28, 2007, provisional application No. 60/943,464, filed on Jun. 12, 2007.

(51) Int. Cl.
*A61B 5/0225* (2006.01)
*A61B 5/024* (2006.01)
*A61B 5/11* (2006.01)
*A61B 5/1455* (2006.01)
*A61B 5/0295* (2006.01)
*A61B 5/0402* (2006.01)
*A61B 5/0452* (2006.01)

(52) U.S. Cl.
CPC ........ *A61B 5/0295* (2013.01); *A61B 5/02133* (2013.01); *A61B 5/02416* (2013.01); *A61B 5/0402* (2013.01); *A61B 5/1118* (2013.01); *A61B 5/14551* (2013.01); *A61B 5/6824* (2013.01); *A61B 5/721* (2013.01); *A61B 5/742* (2013.01); *A61B 5/0452* (2013.01); *A61B 5/7239* (2013.01)

(56) References Cited

U.S. PATENT DOCUMENTS

| | | | |
|---|---|---|---|
| 2007/0066910 A1* | 3/2007 | Inukai | A61B 5/02125 600/513 |
| 2009/0018453 A1 | 1/2009 | Banet et al. | |
| 2009/0069642 A1* | 3/2009 | Gao | A61B 5/02055 600/300 |
| 2009/0306487 A1* | 12/2009 | Crowe | A61B 5/02433 600/322 |
| 2010/0125188 A1* | 5/2010 | Schilling | A61B 5/0002 600/336 |

OTHER PUBLICATIONS

The Office Action and Search Report issued by SIPO in Chinese Patent Application 201510785492.4 dated Aug. 13, 2018—incl Engl lang transl.

\* cited by examiner

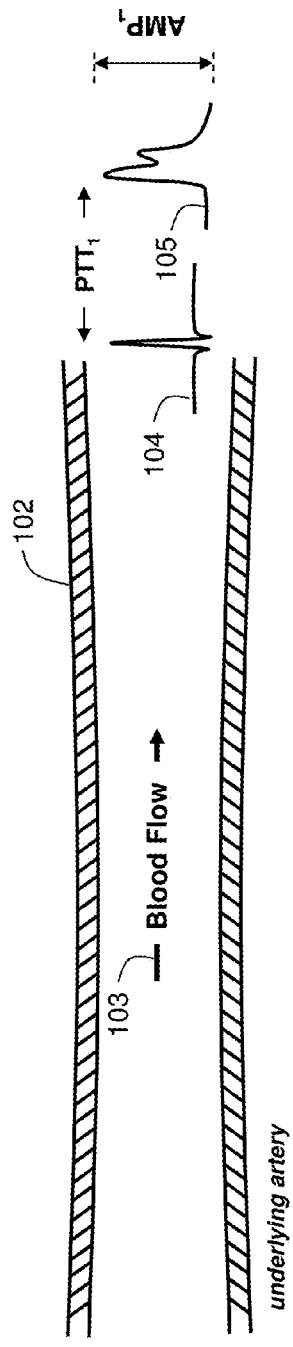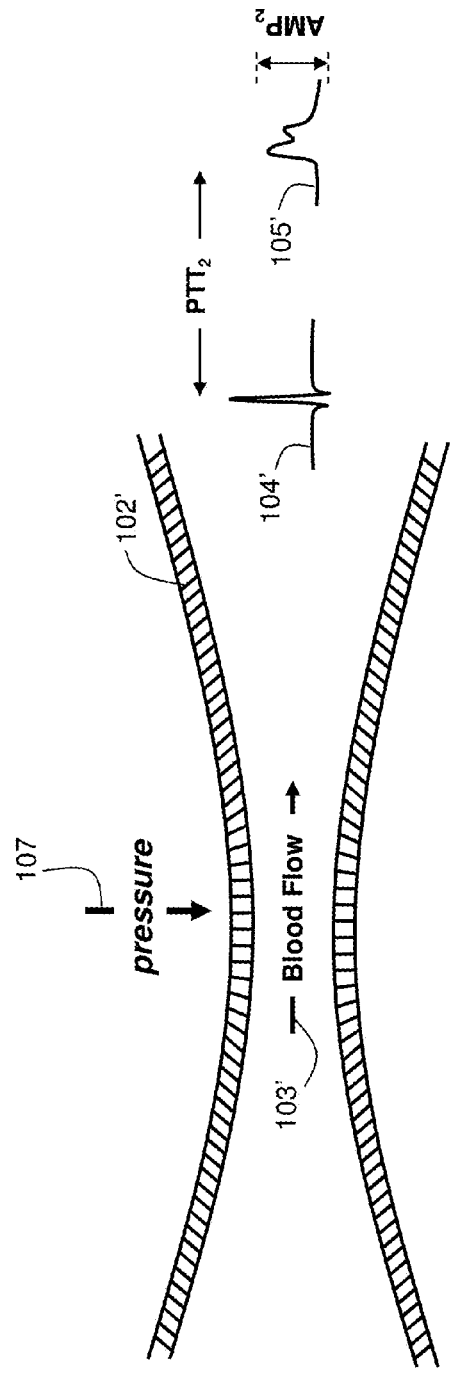

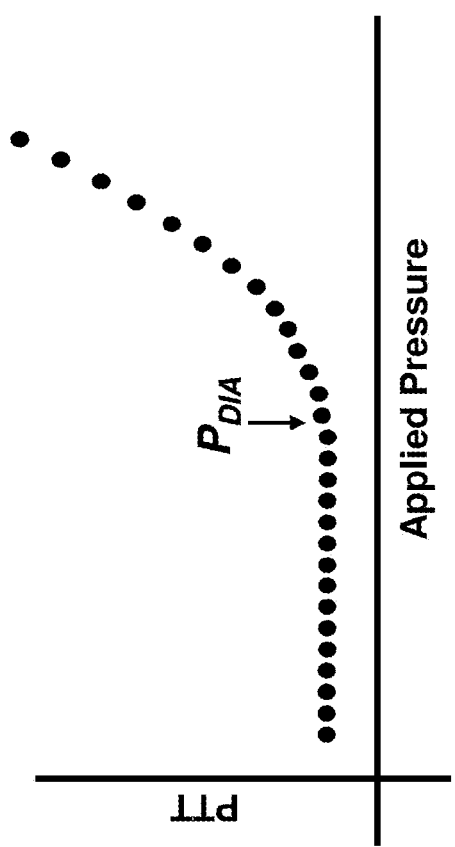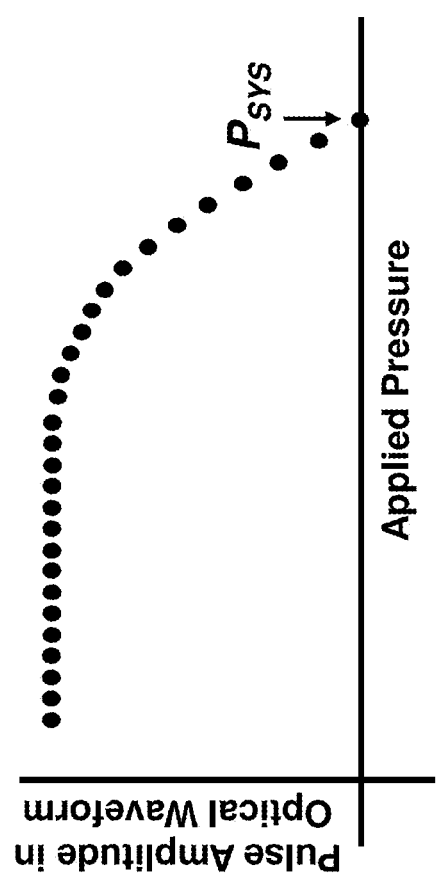

| Calibration Period | SYS DRIFT | DIA DRIFT |
|---|---|---|
| 4 Hours (N = 22) | -0.07 mmHg/hour P = 0.03 | -0.01 mmHg/hour not significant |
| 8 Hours (N = 6) | -0.4 mmHg/hour P = 0.004 | -0.3 mmHg/hour P = 0.0002 |

Fig. 14

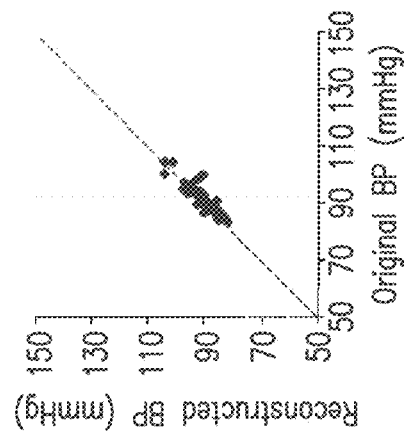
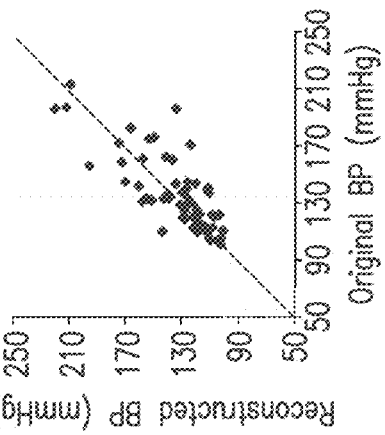
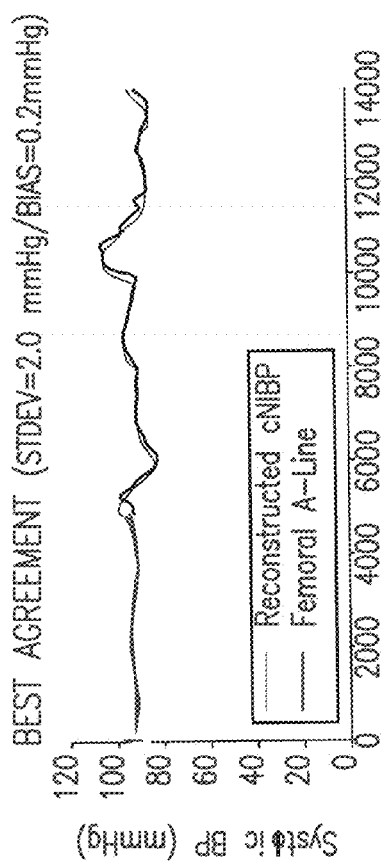
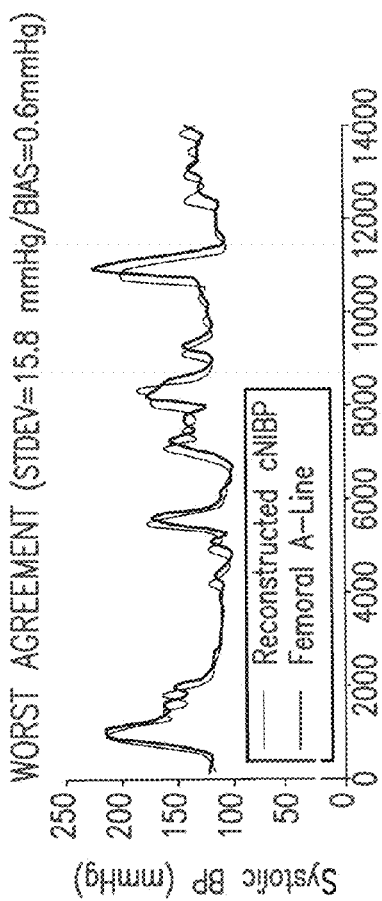

Array Detector

Single-Pixel Detector

BODY-WORN SYSTEM FOR MEASURING CONTINUOUS NON-INVASIVE BLOOD PRESSURE (CNIBP)

CROSS REFERENCES TO RELATED APPLICATIONS

This application is a Continuation of U.S. patent application Ser. No. 12/650,392, filed Dec. 30, 2009, now U.S. Pat. No. 9,668,656, which is a Continuation-in-Part of U.S. patent application Ser. No. 12/138,194, filed Jun. 12, 2008, now U.S. Pat. No. 8,419,649, which claims the benefit of U.S. Provisional Application No. 60/943,464, filed Jun. 12, 2007, and of U.S. Provisional Application No. 60/983,198, filed Oct. 28, 2007; all of which are incorporated herein by reference.

BACKGROUND OF THE INVENTION

Pulse transit time (PTT), defined as the transit time for a pressure pulse launched by a heartbeat in a patient's arterial system, has been shown in a number of studies to correlate to both systolic and diastolic blood pressure. In these studies, PTT is typically measured with a conventional vital signs monitor that includes separate modules to determine both an electrocardiogram (ECG waveform) and pulse oximetry (SpO2). During a PTT measurement, multiple electrodes typically attach to a patient's chest to determine a time-dependent component of the ECG waveform characterized by a sharp spike called the 'QRS complex'. The QRS complex indicates an initial depolarization of ventricles within the heart and, informally, marks the beginning of the heartbeat and a pressure pulse that follows. SpO2 is typically measured with a bandage or clothespin-shaped sensor that attaches to a patient's finger, and includes optical systems operating in both red and infrared spectral regions. A photodetector measures radiation emitted from the optical systems that transmits through the patient's finger. Other body sites, e.g., the ear, forehead, and nose, can also be used in place of the finger. During a measurement, a microprocessor analyses both red and infrared radiation measured by the photodetector to determine time-dependent waveforms corresponding to the different wavelengths called photoplethysmographs ('PG waveforms'). From these a SpO2 value is calculated. Time-dependent features of the PPG waveform indicate both pulse rate and a volumetric absorbance change in an underlying artery (e.g., in the finger) caused by the propagating pressure pulse.

Typical PTT measurements determine the time separating a maximum point on the QRS complex (indicating the peak of ventricular depolarization) and a portion of the PPG waveform (indicating the arrival of the pressure pulse). PTT depends primarily on arterial compliance, the propagation distance of the pressure pulse (which is closely approximated by the patient's arm length), and blood pressure. To account for patient-specific properties, such as arterial compliance, PTT-based measurements of blood pressure are typically 'calibrated' using a conventional blood pressure cuff. Typically during the calibration process the blood pressure cuff is applied to the patient, used to make one or more blood pressure measurements, and then removed. Going forward, the calibration measurements are used, along with a change in PTT, to determine the patient's blood pressure and blood pressure variability. PTT typically relates inversely to blood pressure, i.e., a decrease in PTT indicates an increase in blood pressure.

A number of issued U.S. patents describe the relationship between PTT and blood pressure. For example, U.S. Pat. Nos. 5,316,008; 5,857,975; 5,865,755; and 5,649,543 each describe an apparatus that includes conventional sensors that measure ECG and PPG waveforms, which are then processed to determine PTT.

SUMMARY OF THE INVENTION

This invention provides a technique for continuous measurement of blood pressure (cNIBP), based on PTT, which features a number of improvements over conventional PTT measurements. Referred to herein as the 'Composite Method', the invention uses a body-worn monitor that measures cNIBP and other vital signs, and wirelessly transmits them to a remote monitor, such as a tablet PC, workstation at a nursing station, personal digital assistant (PDA), or cellular telephone. The body-worn monitor features a wrist-worn transceiver that receives and processes signals generated by a network of body-worn sensors. During a measurement these sensors are typically placed on the patient's arm and chest and measure time-dependent ECG, PPG, pressure, and accelerometer waveforms. Sensors within the network typically include a cuff with an inflatable air bladder, at least three electrical sensors (e.g. ECG electrodes), three accelerometers, and an optical sensor (e.g., a light source and photodiode) typically worn around the patient's thumb. They measure signals that are processed according to the Composite Method to determine blood pressure, and with other algorithms to determine vital signs such as SpO2, respiration rate, heart rate, temperature, and motion-related properties such as motion, activity level, and posture. The body-worn monitor then wirelessly transmits this information (typically using a two-way wireless protocol, e.g. 802.15.4 or 802.11) to the remote monitor. The monitor displays both vital signs and the time-dependent waveforms. Both the monitor and the wrist-worn transceiver can additionally include a barcode scanner, touch screen display, camera, voice and speaker system, and wireless systems that operate with both local-area networks (e.g. 802.11 or 'WiFi' networks) and wide-area networks (e.g. the Sprint network) to transmit and display information.

The Composite Method includes both pressure-dependent and pressure-free measurements. It is based on the discovery that PTT and the PPG waveform used to determine it are strongly modulated by an applied pressure. During a pressure-dependent measurement, also referred to herein as an 'indexing measurement', two events occur as the pressure gradually increases to the patient's systolic pressure: 1) PTT increases, typically in a non-linear manner, once the applied pressure exceeds diastolic pressure; and 2) the magnitude of the PPG's amplitude systematically decreases, typically in a linear manner, as the applied pressure approaches systolic pressure. The applied pressure gradually decreases blood flow and consequent blood pressure in the patient's arm, and therefore induces the pressure-dependent increase in PTT. Each of the resulting pairs of PTT/blood pressure readings measured during the period of applied pressure can be used as a calibration point. Moreover, when the applied pressure equals systolic blood pressure, the amplitude of the PPG waveform is completely eliminated, and PTT is no longer measurable. Collectively analyzing both PTT and the PPG waveform's amplitude over a suitable range, along with the pressure waveform using techniques borrowed from conventional oscillometry, yields the patient's systolic (SYS), diastolic (DIA), and mean (MAP) arterial pressures, along with a patient-specific slope relating PTT and MAP. From these parameters the patient's cNIBP can be determined without using a conventional cuff.

A combination of several algorithmic features improves the efficacy of the Composite Method over conventional PTT measurements of cNIBP. For example, sophisticated, real-time digital filtering removes high-frequency noise from the PPG waveform, allowing its onset point to be accurately detected. When processed along with the ECG waveform, this ensures measurement of an accurate PTT and, ultimately, cNIBP value. The pressure-dependent indexing method, which is made during inflation of the arm-worn cuff, yields multiple data points relating PTT and blood pressure during a short (~60 second) measurement. Processing of these data points yields an accurate patient-specific slope relating PTT to cNIBP. Inclusion of multiple accelerometers yields a variety of signals that can determine features like arm height, motion, activity level, and posture that can be further processed to improve accuracy of the cNIBP calculation, and additionally allow it to be performed in the presence of motion artifacts. And a model based on femoral blood pressure, which is more representative of pressure in the patient's core, can reduce effects such as 'pulse pressure amplification' that can elevate blood pressure measured at a patient's extremities.

The Composite Method can also include an 'intermediate' pressure-dependent measurement wherein the cuff is partially inflated. This partially decreases the amplitude of the PPG waveform in a time-dependent manner. The amplitude's pressure-dependent decrease can then be 'fit' with a numerical function to estimate the pressure at which the amplitude completely disappears, indicating systolic pressure.

For the pressure-dependent measurement, a small pneumatic system attached to the cuff inflates the bladder to apply pressure to an underlying artery according to the pressure waveform. The cuff is typically located on the patient's upper arm, proximal to the brachial artery, and time-dependent pressure is measured by an internal pressure sensor, such as an in-line Wheatstone bridge or strain gauge, within the pneumatic system. The pressure waveform gradually ramps up in a mostly linear manner during inflation, and then slowly rapidly deflates through a 'bleeder valve' during deflation. During inflation, mechanical pulsations corresponding to the patient's heartbeats couple into the bladder as the applied pressure approaches DIA. The mechanical pulsations modulate the pressure waveform so that it includes a series of time-dependent oscillations. The oscillations are similar to those measured with an automated blood pressure cuff using oscillometry, only they are measured during inflation rather than deflation. They are processed as described below to determine a 'processed pressure waveform', from which MAP is determined directly, and SYS and DIA are determined indirectly.

Pressure-dependent measurements performed on inflation have several advantages to similar measurements performed on deflation, which are convention. For example, inflation-based measurements are relatively fast and comfortable compared to those made on deflation. Most conventional cuff-based systems using deflation-based oscillometry take roughly 4 times longer than the Composite Method's pressure-dependent measurement. Inflation-based measurements are possible because of the Composite Method's relatively slow inflation speed (typically 5-10 mmHg/second) and high sensitivity of the pressure sensor used within the body-worn monitor. Moreover, measurements made during inflation can be immediately terminated once systolic blood pressure is calculated. In contrast, conventional cuff-based measurements made during deflation typically apply a pressure that far exceeds the patient's systolic blood pressure; pressure within the cuff then slowly bleeds down below DIA to complete the measurement.

Pressure-free measurements immediately follow the pressure-dependent measurements, and are typically made by determining PTT with the same optical and electrical sensors used in the pressure-dependent measurements. Specifically, the body-worn monitor processes PTT and other properties of the PPG waveform, along with the patient-specific slope and measurements of SYS, DIA, and MAP made during the pressure-dependent measurement, to determine cNIBP.

In addition to blood pressure, the body-worn monitor measures heart rate (HR), SpO2, and respiratory rate from components of the ECG, PPG, and accelerometer waveforms. A body-worn thermocouple measures temperature. These measurements, along with those used to process accelerometer waveforms to determine motion, posture, and activity level, are made using algorithms described below.

In one aspect, the invention provides a body-worn monitor, described in detail below, which measures cNIBP from an ambulatory patient according to the Composite Method. The body-worn monitor features: (1) a pressure-delivery and sensor system that applies a variable pressure to the patient's arm and, in response, measures a time-dependent pressure waveform; (2) a first sensor (e.g. an optical sensor) that generates a first time-dependent waveform representing a flow of blood within the patient; and (3) a second sensor (e.g. an ECG circuit and electrodes) that generates a second time-dependent waveform representing contractile properties of the patient's heart. A processing component receives information from these sensors, and processes it to: (1) determine a PTT between features in the first and second waveforms; (2) determine a mathematical relationship between PTT and blood pressure in the patient's core region (e.g. femoral artery); and iii) analyze a PTT and the mathematical relationship to generate a blood pressure indicative of the patient's core region. The processing component is typically located in the wrist-worn transceiver.

In embodiments, the ECG circuit within the body-worn monitor features a single circuit (e.g. an ASIC) that collects electrical signals from a series of body-worn electrodes and coverts these signals into a digital ECG waveform. Such a circuit is typically worn directly on the patient's chest, and connects to the wrist-worn transceiver through a digital, serial interface (e.g. an interface based on a 'control area network', or 'CAN', system). The optical sensor typically includes optics for measuring signals relating to both cNIBP and SpO2, and typically features a ring-like form factor that comfortably wraps around the base of the patient's thumb. All of these systems are described in detail below.

In embodiments, both the first and second sensors feature transducers for measuring optical, pressure, acoustic, and electrical impedance signals, as well as electrical components for measuring ECG waveforms. In general, PTT can be determined from various combinations of these signals, e.g. between any two signals measured by a transducer, or between an ECG waveform and a second signal measured by a transducer. In preferred embodiments, the first sensor measures a PPG waveform, the second sensor measures an ECG waveform, and the processing component determines PTT from a QRS complex in an ECG waveform and an onset point of the PPG waveform. The processing component then analyzes PTT measured as pressure is applied to determine its relationship to MAP in the patient's femoral artery. In embodiments, this relationship is characterized by the following Equation, or a mathematical derivative thereof:

$$MAP_{femoral} = (m_{femoral} \times PTT) - (m_{femoral} \times PTT_{INDEX}) + MAP_{INDEX}$$

wherein $MAP_{femoral}$ represents blood pressure in the patient's femoral artery, PTT represents pulse transit time measured from the first and second waveforms, $PTT_{INDEX}$ represents a pulse transit time determined before PI I (and typically immediately before the pressure-dependent indexing measurement), $m_{femoral}$ represents a mathematical slope representing a relationship between $MAP_{femoral}$ and PTT, and $MAP_{INDEX}$ represents a mean arterial pressure determined from the time-dependent pressure waveform. In the Equation above, $m_{femoral}$ is typically determined by collectively processing the first, second, and pressure waveforms. For example, it can be determined by processing a set of PTT values measured while time-dependent pressure is applied to the patient's arm, and then fitting the set with a linear equation to estimate a patient-specific relationship between PTT and MAP. This relationship, which is determined during the pressure-dependent indexing measurement, forms part of a 'calibration' for cuffless, PTT-based cNIBP measurement made afterwards. Other calibration parameters determined during the indexing measurement are SYS, DIA, and relationships between these parameters and MAP. These values are determined directly from a pressure waveform, typically measured during inflation using techniques derived from oscillometry. In embodiments, during an indexing measurement a digital filter, typically implemented with a software-based algorithm, processes the time-dependent pressure waveform to determine a 'processed pressure waveform'. The digital filter, for example, can be a 2-stage filter featuring a digital bandpass filter, followed by a digital low-pass filter. From the processed pressure waveform SYS, DIA, and MAP can be determined.

In other embodiments, the relationship between SYS, DIA, and MAP depends on the patient's HR, which is typically determined from either the ECG or PPG waveform. In still other embodiments, the relationship between PTT and MAP is non-adjustable and determined beforehand, e.g. from a group of patients in a clinical study. During an actual measurement, such a relationship is typically used as a default case when a patient-specific relationship cannot be accurately determined (because, e.g., of PPG or ECG waveforms corrupted by motion-related noise). Typically the relationship between PTT and MAP in the patient's femoral artery is between 0.5 mmHg/ms and 1.5 mmHg/ms.

In another aspect, the patient-specific indexing measurement involves estimating an 'effective MAP' in the patient's arm that varies with pressure applied by the pressure-delivery system. The effective MAP is the difference between MAP determined during the inflation in the indexing measurement and a pressure-induced blood pressure change, caused by an arm-worn cuff featuring an inflatable bladder. In embodiments, the pressure-induced blood pressure change is defined by the following equation or a mathematical derivative thereof:

$$\Delta MAP(P) = F \times (P_{applied} - DIA_{INDEX})$$

where $\Delta MAP(P)$ is the pressure-induced blood pressure change, $P_{applied}$ is pressure applied by the pressure-delivery system during inflation, $DIA_{INDEX}$ is the diastolic pressure determined from the processed pressure waveform during the indexing measurement, and F is a mathematical constant.

In embodiments, the indexing measurement is performed once every 4 hours or more, and a PTT-based cNIBP measurement is performed once every 1 second or less. Typically, PTT values are averaged from a set of values collected over a time period between, typically ranging from 10 to 120 seconds. The average is typically a 'rolling average' so that a new value, determined over the averaging period, can be displayed relatively frequently (e.g. every second).

In another aspect, the invention provides a method for monitoring a blood pressure value from a patient, which features determining a PTT value from a patient, as described above, from PPG and ECG waveforms. Additionally, HR is determined by analyzing QRS complexes in the ECG waveform. During the measurement, the processing component determines a mathematical relationship between HR (or a parameter calculated therefrom), and PTT (or a parameter calculated therefrom). At a later point in time, the processing component uses the mathematical relationship and a current value of HR to estimate PTT and, ultimately, a based blood pressure value. This method would be deployed, for example, when motion-related noise corrupts the PPG waveform (which is relatively sensitive to motion), but not the ECG waveform (which is relatively immune to motion).

In embodiments, the method measures a first set of HR values and a second set of PTT values, and then processes the first and second sets to determine the mathematical relationship between them. The first and second sets are typically measured prior to measuring the HR used to estimate PTT, and are typically collected over a time period ranging between 5 and 60 seconds. Paired HR/PTT values collected during the time period are then analyzed, typically by fitting them using a linear regression algorithm, to determine a mathematical relationship relating HR to PTT. Alternatively a non-linear fitting algorithm, such as the Levenburg-Marquardt algorithm, can be used to determine a non-linear relationship between HR and PTT. The non-linear relationship can be characterized, e.g., by a second or third-order polynomial, or by an exponential function.

As described above, this algorithm is typically performed when a patient's motion makes it difficult or impossible to accurately calculate PTT from the PPG waveform. The algorithm can be initiated when analysis of a pulse in the PPG waveform indicates PTT cannot be measured. Alternatively, the algorithm is initiated when analysis of at least one 'motion waveform' (e.g. an accelerometer waveform generated from one or more signals from an accelerometer) indicates that the PPG waveform is likely corrupted by motion. Analysis of the motion waveform can involve comparing a portion of it to a predetermined threshold, or analyzing it with a mathematical model, to determine if an accurate PTT can be calculated.

In a related aspect, the invention provides another algorithm that allows PTT-based cNIBP to be determined in the presence of motion. In this case, rather than estimating PTT from HR using a mathematical model, the algorithm 'reconstructs' motion-corrupted pulses in the PPG waveform through analysis of separate PPG waveforms measured simultaneously with two separate light sources. A pulse oximeter sensor, such as that included in the body-worn monitor described in detail below, includes a first light source operating in a red spectral region (between 590 and 700 nm, and preferably about 660 nm), and a second light source operating in the infrared spectral region (between 800 and 1000 nm, and preferably around 905 nm), and can therefore be used for this purpose.

The algorithm features: 1) collectively processing unique PPG waveforms to generate a processed signal; 2) processing the processed signal with a digital filter to generate a filtered signal; 3) analyzing the filtered signal to determine a feature related to blood pressure; and 4) analyzing the feature related to blood pressure to determine the blood pressure value. In embodiments, the processing component is programmed to collectively process the first and second signals by subtracting one signal from the other, or dividing one signal into the other, to generate the processed signal. This signal is then filtered with a digital bandpass filter, typically characterized by a passband between 0.01→5.0 Hz, to generate the filtered signal. The filtered signal is typically relatively free of motion artifacts, and yields an onset point which can be combined with an ECG QRS complex to determine PTT and then cNIBP. As described above, this algorithm can be initiated by processing an accelerometer waveform which indicates that a patient is moving, or by processing the PPG waveforms to determine that they are corrupted in any way. In other embodiments, steps in the algorithm are rearranged so that the corrupted PPG waveforms are first filtered with a digital bandpass filter, and then these filtered waveforms are subtracted from each other or divided into each other, and then processed to determine an onset point.

In another aspect, the body-worn monitor's optical sensor described above features a detector that includes at least two pixel elements, each configured to generate a unique signal. A processing component within the monitor is configured to: (1) analyze a signal generated by a first pixel element; (2) analyze a signal generated by a second pixel element; (3) analyze a signal indicating motion, e.g. an accelerometer waveform; (4) based on analysis of the motion signal, select a signal from at least one of the pixel elements characterized by a relatively low degree of motion corruption; and (5) analyze the selected signal to determine a vital sign value, e.g. cNIBP.

In embodiments, the multi-pixel detector features at least a 3×3 array of pixels, each containing a photodetector. In this case the optical sensor is integrated with a circuit configured to de-multiplex signals from the multi-pixel detector. The processor in the body-worn monitor can be programmed to analyze the motion signal and a signal from each pixel element to determine the signal that has the lowest correlation to the motion signal, indicating that the signal is characterized by a relatively low degree of motion corruption. Correlation, for example, can be determined using standard algorithms known in the art, such as algorithms that determine cross-correlation between two sequences of data points. Such algorithms can yield a Gaussian-type waveform, with the amplitude of the waveform increasing with correlation. The waveform can then be compared to a series of metrics to determine a numerical figure of merit indicating the degree of correlation. Alternatively, the processor is programmed to analyze the motion signal to determine a measurement period when patient movement is relatively low, and then measure a signal from each pixel element. In both cases, the signal from each pixel element represents a PPG waveform featuring a sequence of pulses, each characterized by an onset point. When combined with an ECG QRS complex, this waveform can yield a PTT as described above. In embodiments the multi-pixel detector is included in the thumb-worn sensor described in detail below. Alternatively, it is incorporated in a flexible patch configured to be worn on the patient's forehead. In this case the flexible patch connects to a body-worn transceiver that is similar to the wrist-worn transceiver in both form and function.

BRIEF DESCRIPTION OF THE DRAWINGS

FIG. 1A shows a schematic drawing indicating the Composite Method's pressure-free measurements;

FIG. 1B shows a schematic drawing indicating the Composite Method's pressure-dependent measurements;

FIG. 2A shows a graph of PTT;

FIG. 2B shows a graph of the amplitude of the PPG waveform measured as a function of pressure;

FIG. 14 shows a table of drift of the SYS and DIA measurements made according to the Composite Method corresponding, respectively, to 4 and 8-hour indexing periods;

FIG. 20A shows time-dependent SYS waveforms made using a femoral A-line (dark gray) and reconstructed using the algorithm shown in FIGS. 18 and 19 to yield the best and worst results for the 23 clinical subjects;

FIG. 20B shows correlation plots generated using data from FIGS. 20A and 21A;

FIG. 21A shows show time-dependent SUS waveforms made using a femoral A-line (dark gray) and reconstructed using the algorithm shown in FIGS. 18 and 19 to yield the worst results for the 23 clinical subjects;

FIG. 21B shows correlation plots generated using data from FIGS. 20A and 21A;

DETAILED DESCRIPTION OF THE INVENTION

Theory of the Composite Method

Figure 3A:
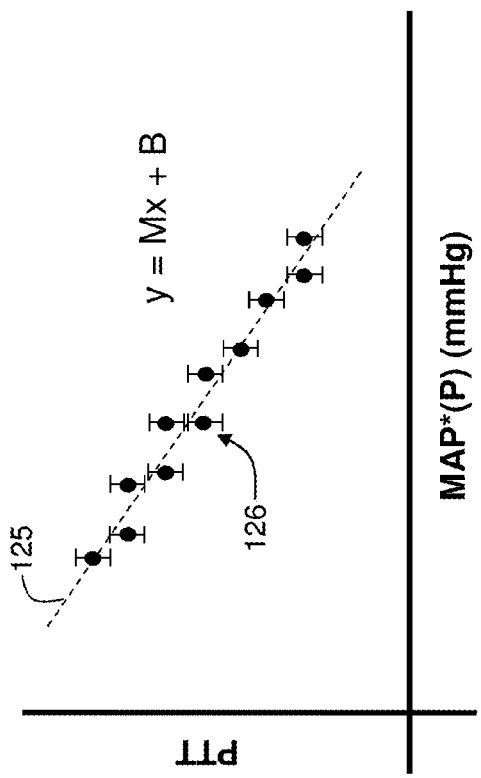
FIG. 3A shows a graph of PTT measured as a function of 'effective' mean arterial blood pressure (MAP*(P)) determined using the Composite Method's pressure-dependent measurement.

FIGS. 1A and 1B show schematic drawings of the Composite Method's pressure-free (FIG. 1A) and pressure-dependent (FIG. 1B) measurements. Working in concert, these measurements accurately determine the patient's cNIBP for an extended time without requiring an external calibration device, e.g., a conventional blood pressure cuff. During a measurement, the patient wears a body-worn monitor attached to a disposable cuff and collection of optical, electrical, motion, and temperature sensors. These sensors measure signals for both the pressure-dependent and pressure-free measurements. The co-pending patent applications, the contents of which are fully incorporated herein by reference, describe earlier embodiments of this measurement: DEVICE AND METHOD FOR DETERMINING BLOOD PRESSURE USING 'HYBRID' PULSE TRANSIT TIME MEASUREMENT (U.S. Ser. No. 60/943,464; filed Jun. 12, 2007); VITAL SIGN MONITOR FOR CUFFLESSLY MEASURING BLOOD PRESSURE USING A PULSE TRANSIT TIME CORRECTED FOR VASCULAR INDEX (U.S. Se. No. 60/943,523; filed Jun. 12, 2007); and VITAL SIGN MONITOR FOR MEASURING BLOOD PRESSURE USING OPTICAL, ELECTRICAL, AND PRESSURE WAVEFORMS (U.S. Ser. No. 12/138,194; filed Jun. 12, 2008). A microprocessor in the body-worn monitor processes the PPG and ECG waveforms to determine PTT, which is used in both measurements of the Composite Method to determine cNIBP, as is described in more detail below.

The cuff includes an air bladder which, when pressurized with a pneumatic system, applies a pressure 107 to an underlying artery 102, 102'. An electrical system featuring at least 3 electrodes coupled to an amplifier/filter circuit within cabling attached to the wrist-worn transceiver measures an ECG waveform 104, 104' from the patient. Three electrodes (two detecting positive and negative signals, and one serving as a ground) are typically required to detect the necessary signals to generate an ECG waveform with an adequate signal-to-noise ratio. At the same time, an optical system featuring a transmissive or, optionally, reflective optical sensor measures a PPG waveform 105, 105' featuring a series of 'pulses', each characterized by an amplitude of $AMP_{1/2}$, from the patient's artery. The preferred measurement site is typically near small arteries in the patient's thumb, such as the princeps pollicis artery. A microprocessor and analog-to-digital converter within the wrist-worn transceiver detects and analyzes the ECG 104, 104' and PPG 105, 105' waveforms to determine both $PTT_1$ (from the pressure-free measurement) and $PTT_2$ (from the pressure-dependent measurement). Typically the microprocessor determines both $PTT_1$ and $PTT_2$ by calculating the time difference between the peak of the QRS complex in the ECG waveform 104, 104' and the foot (i.e. onset) of the PPG waveform 105, 105'.

The invention is based on the discovery that an applied pressure (indicated by arrow 107) during the pressure-dependent measurement affects blood flow (indicated by arrows 103, 103') in the underlying artery 102, 102'. Specifically, the applied pressure has no affect on either $PTT_2$ or $AMP_2$ when it is less than a diastolic pressure within the artery 102, 102'. When the applied pressure 107 reaches the diastolic pressure it begins to compress the artery, thus reducing blood flow and the effective internal pressure. This causes $PTT_2$ to systematically increase relative to $PTT_1$, and $AMP_2$ to systematically decrease relative to $AMP_1$. $PTT_2$ increases and $AMP_2$ decreases (typically in a linear manner) as the applied pressure 107 approaches the systolic blood pressure within the artery 102, 102'. When the applied pressure 107 reaches the systolic blood pressure, $AMP_2$ is completely eliminated and $PTT_2$ consequently becomes immeasurable.

During a measurement the patient's heart generates electrical impulses that pass through the body near the speed of light. These impulses accompany each heartbeat, which then generates a pressure wave that propagates through the patient's vasculature at a significantly slower speed. Immediately after the heartbeat, the pressure wave leaves the heart and aorta, passes through the subclavian artery, to the brachial artery, and from there through the radial and ulnar arteries to smaller arteries in the patient's fingers. Three disposable electrodes located on the patient's chest measure unique electrical signals which pass to an amplifier/filter circuit within the body-worn monitor. Typically, these electrodes attach to the patient's chest in a 1-vector 'Einthoven's triangle' configuration to measure unique electrical signals. Within the body-worn monitor, the signals are processed using the amplifier/filter circuit to determine an analog electrical signal, which is digitized with an analog-to-digital converter to form the ECG waveform and then stored in memory. The optical sensor typically operates in a transmission-mode geometry, and includes an optical module featuring an integrated photodetector, amplifier, and pair of light sources operating at red (~660 nm) and infrared (~905 nm) wavelengths. These wavelengths are selected because they are effective at measuring PPG waveforms with high signal-to-noise ratios that can additionally be processed to determine SpO2. In alternative embodiments, an optical sensor operating in a reflection-mode geometry using green (~570 nm) wavelengths can be used in place of the transmission-mode sensor. Such a sensor has the advantage that it can be used at virtually any location on the patient's body. The green wavelength is chosen because it is particularly sensitive to volumetric absorbance changes in an underlying artery for a wide variety of skin types when deployed in a reflection-mode geometry, as described in the following co-pending patent application, the entire contents of which are incorporated herein by reference: SYSTEM FOR MEASURING VITAL SIGNS USING AN OPTICAL MODULE FEATURING A GREEN LIGHT SOURCE (U.S. Ser. No. 11/307,375; filed Feb. 3, 2006).

The optical sensor detects optical radiation modulated by the heartbeat-induced pressure wave, which is further processed with a second amplifier/filter circuit within the wrist-worn transceiver. This results in the PPG waveform, which, as described above, includes a series of pulses, each corresponding to an individual heartbeat. Likewise, the ECG waveforms from each measurement feature a series of sharp, 'QRS' complexes corresponding to each heartbeat. As described above, pressure has a strong impact on amplitudes of pulses in the PPG waveform during the pressure-dependent measurement, but has basically no impact on the amplitudes of QRS complexes in the corresponding ECG waveform. These waveforms are processed as described below to determine blood pressure.

The Composite Method performs an indexing measurement once every 4-8 hours using inflation-based oscillometry. During the indexing measurement, a linear regression model is used to relate the pressure applied by the cuff to an 'effective MAP' (referred to as MAP*(P) in FIG. 3A) representing a mean pressure in the patient's arm. MAP*(P) and the PTT value associated with it vary tremendously during an inflationary process. As shown in FIG. 3A, this results in a unique set of MAP*(P)/PTT paired data points which can be extracted for each heartbeat occurring as the applied pressure ramps from DIA to SYS. This means calibration can be performed with a single, inflation-based measurement that typically takes between 40 -60 seconds. At a recommended inflation rate (approximately 3-10 mmHg/second, and most preferably about 5 mmHg/second) this typically yields between 5-15 data points. These are the data points analyzed with the linear regression model to determine the patient-specific slope. Blood pressure values ($SYS_{INDEX}$, $MAP_{INDEX}$, and $DIA_{INDEX}$) and the ratios between them ($R_{SYS}=SYS_{INDEX}/MAP_{INDEX}$; $R_{DIA}=DIA_{INDEX}/MAP_{INDEX}$) determined during the inflation-based measurement are also used in this calculation, and then for subsequent pressure-free measurements.

A stable PTT value is required for accurate indexing, and thus PTT is measured from both the ECG and PPG waveforms for each heartbeat over several 20-second periods prior to inflating the pump in the pneumatic system. The PTT values are considered to be stable, and suitable for the indexing measurement, when the standard deviation of the average PTT values from at least three 20-second periods ($PTT_{STDEV}$) divided by their mean ($PTT_{MEAN}$) is less than 7%, i.e.:

$$\frac{PTT_{STDEV}}{PTT_{MEAN}} < 0.07 \tag{1}$$

When this criterion is met the pump is automatically inflated, and he patient-specific slope is then determined as described above. This process is typically repeated every 4-8 hours. Once determined, the slope is analyzed with a series of empirical metrics to ensure that it is both realistic and consistent with those determined with previous trials. An unrealistic personal slope would result, for example, if a motion-related artifact occurred during the indexing measurement. If either the value or the linear fit used to determine it fails to meet these metrics, then a default slope, determined from analyzing arterial line data collected from a large number of patients, is used in its place. Additionally, the above-described model tends to yield relatively inaccurate results for patients with very low slopes (i.e., slopes less than −0.22 mmHg/ms), and for this case a secondary model is therefore used. This model, which is typically determined experimentally on patients having particularly low personal slopes, relates the personal slope to pulse pressure.

During an actual pressure-dependent indexing measurement, the body-worn monitor collects data like that shown in FIGS. 2A and 2B, for an individual patient. During a measurement, the microprocessor analyzes the variation between applied pressure and PTT, shown graphically in FIG. 2A, to estimate the relationship between blood pressure and PTT. As shown in Equation (2), below, this relationship is best described with a mathematical model that first estimates how the patient's 'effective' mean arterial blood pressure (MAP*(P)) varies with applied pressure ($P_{applied}$). The model assumes that pressure applied by the cuff occludes the patient's brachial artery, and thus temporarily decreases blood flow. This, in turn, increases blood pressure directly underneath the cuff, and reduces blood pressure in the downstream radial, ulnar, and finger arteries. The net effect is a temporary, pressure-dependent reduction in the patient's mean arterial blood pressure (MAP), indicated in Equation (2) as $\Delta MAP(P)$, during the pressure-dependent measurement. An empirically determined factor (F) accounts for the ratio between the region of increased blood pressure (underneath the cuff; approximately 10 cm) and the larger region of decreased blood pressure (the length of the arm downstream from the cuff; approximately 50 cm). F is typically between 0.6 and 0.9, and is preprogrammed into the algorithm prior to measurement.

$\Delta MAP(P) = F \times (P_{applied} - DIA_{INDEX})$ $$MAP^*(P) = MAP_{INDEX} - \Delta MAP(P) \quad (2)$$

Using Equation (2), paired values of PTT and MAP*(P) are determined for each heartbeat as the applied pressure increases from $DIA_{INDEX}$ to $MAP_{INDEX}$. This approach yields multiple data points during a single pressure-dependent measurement that can then be fit with a mathematical function (e.g. a linear function) relating PTT to MAP. Typically these parameters are inversely related, i.e. PTT gets shorter and blood pressure increases. In typical embodiments, therefore, an inverse linear relationship determined during the pressure-dependent indexing measurement is then used during subsequent pressure-free measurements to convert the measured PTT into blood pressure values.

In Equation (2), the values for $DIA_{INDEX}$ and $MAP_{INDEX}$ are determined with an oscillometric blood pressure measurement during inflation. $SYS_{INDEX}$ can either be determined indirectly during the oscillometric blood pressure measurement, or directly by analyzing the pressure-dependent pulse amplitude in the PPG waveform. In this embodiment, as shown in FIG. 2B, the pulse amplitude will gradually reduce with applied pressure, and eventually disappears when this pressure is equal to SYS. A conventional peak-detecting algorithm running on the microprocessor can thus detect the onset of the optical pulse amplitude shown in FIG. 2B to make a direct measurement of systolic blood pressure. Alternatively, a 'fitting' algorithm can model the systematic decrease in pulse amplitude with applied pressure with a mathematical function (e.g. a linear function) to estimate systolic blood pressure.

Figure 3B:
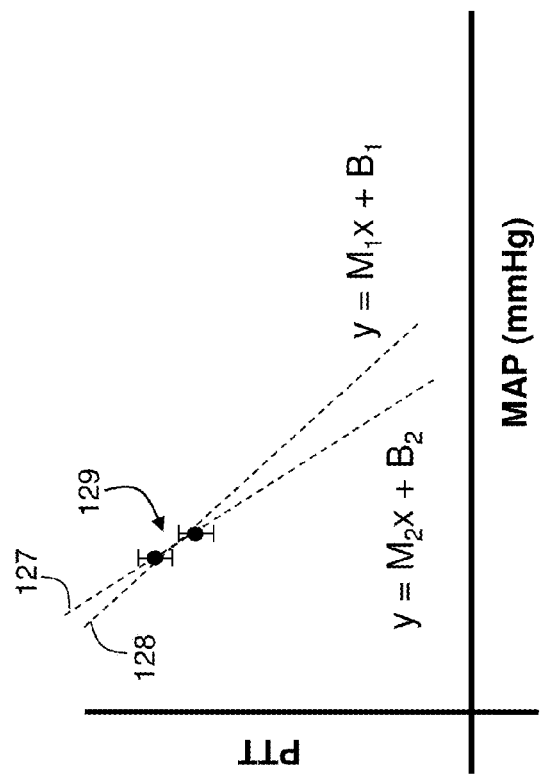
FIG. 3B shows a graph of PTT measured as a function of mean arterial blood pressure (MAP) determined using a conventional blood pressure measurement of the prior art.

FIGS. 3A and 3B show graphs of PTT as a function MAP*(P) (FIG. 3A) and MAP (FIG. 3B) for a single patient. Each data point 126, 129 in the graphs includes error bars representing an approximate measurement error. In FIG. 3A, the data points 126 are determined during a single, 30-second pressure-dependent measurement of the Composite Method; each data point represents PTT and MAP*(P) values for an individual heartbeat. These data points are derived, for example, by combining measurements similar to those shown in FIG. 2A (PTT as a function of applied pressure) and Equation (2) (MAP*(P) calculated from applied pressure). In contrast, the two data points 129 in FIG. 3B are derived by simply measuring PTT and MAP during separate blood pressure measurements. Each measurement normally takes about 60 seconds to complete; they are ideally done at separate points in time when the patient's blood pressure (and corresponding PTT) differs by a measurable amount.

The two graphs illustrate the advantages of determining a patient-specific relationship between PTT and blood pressure during the Composite Method's pressure-dependent measurement. As shown in FIG. 3A, the data points 126 vary over approximately a relatively large range in blood pressure (typically 15 mmHg or more); they are typically tightly correlated, and, despite any measurement error, can be easily fit with a single linear equation (y=Mx+B) shown by the dashed line 125. In contrast, if the patient's blood pressure is relatively stable, the two data points 129 of FIG. 3B can have similar values, even if they are measured several hours apart. These two values can yield fits with different linear equations ($y=M_1 x+B_1$ and $y=M_2 x +B_2$ and) even when the measurement error is low. Using an inaccurate linear equation in this instance can, in turn, result in an inaccurate relationship between PTT and blood pressure. Ultimately this adds error to the PTT-based blood pressure measurement.

Figures 4A, 4B:
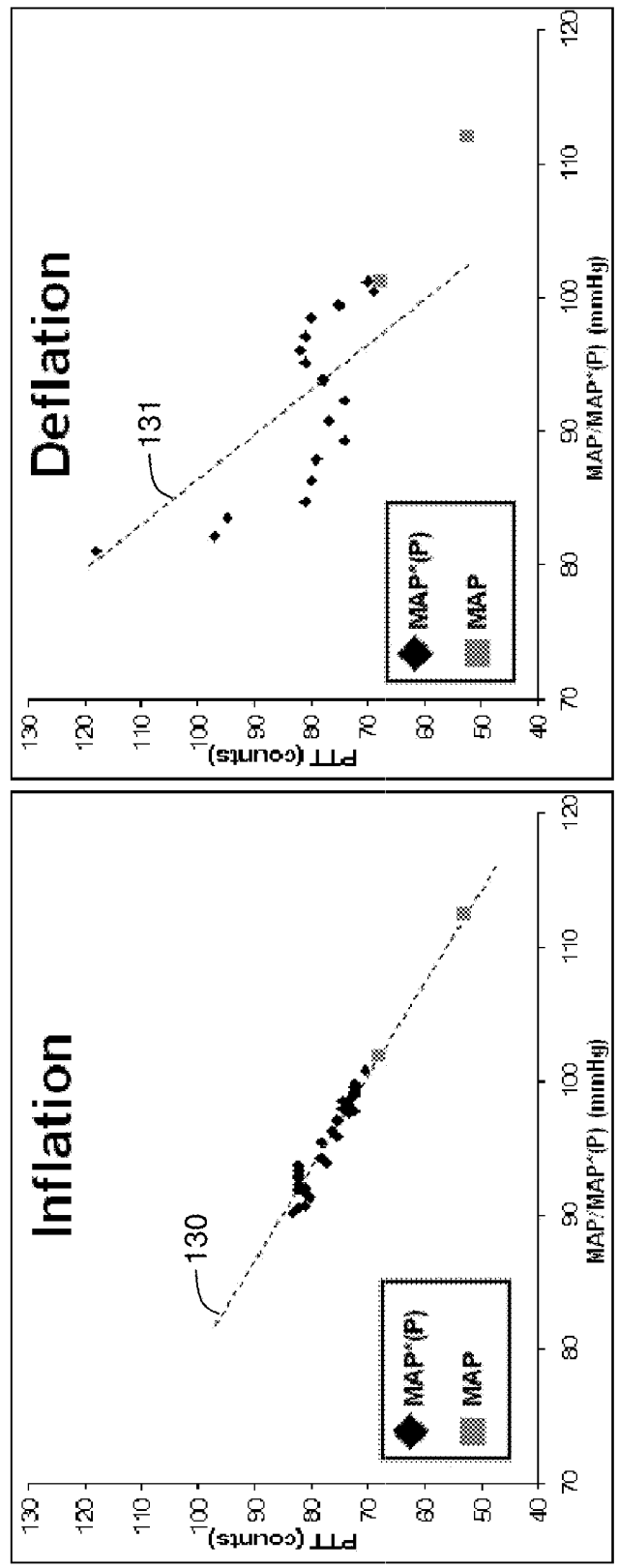
FIG. 4A shows a graph of PTT measured as a function of both MAP*(P) (measured during inflation using the Composite Method's pressure-dependent measurement) and MAP (measured for two separate blood pressure values using oscillometry) for a single patient.
FIG. 4B shows a graph of PTT measured as a function of both MAP*(P) (measured during deflation using the Composite Method's pressure-dependent measurement) and MAP (measured for two separate blood pressure values) for a single patient.

FIGS. 4A and 4B show actual PTT vs. MAP*(P) and MAP data, measured for a single patient, during a pressure-dependent measurement that uses inflation (FIG. 4A) and deflation (FIG. 4B). In the figures the triangles indicate PTT vs. MAP*(P) determined during the Composite Method's pressure-dependent indexing measurement. These data represent a calibration of the blood pressure measurement. The squares indicate subsequent, measurements wherein MAP is determined using an automated blood pressure cuff, and PTT is determined using the body-worn monitor described herein. As is clear from the figures, the values of PTT vs. MAP*(P) measured during inflation (FIG. 4A) have a tight, well-correlated distribution compared to those measured during deflation (FIG. 4B). This indicates that a calibration determined from a pressure-dependent measurement made during inflation is likely more accurate than one made during deflation. Without being bound by any theory, this discrepancy may be due an inflation-based pressure-dependent measurement that gradually reduces blood flow in an underlying artery until it is ultimately occluded. In contrast, a deflation-based measurement first fully occludes the artery, and then gradually reduces the occlusion as the cuff deflates. Dammed-up blood rapidly flows through the artery during this process. This increase in blood flow may cause turbulence and other complicated hemodynamic events that add variability to the PTT value. Such processes are likely not present during an inflation-based measurement.

In FIG. 4A, a linear fit to the values of PTT vs. MAP*(P), shown by the dashed line 130, also fits the measurements of PTT vs. MAP. This indicates a calibration determined during the pressure-dependent measurement (triangles) can be used to accurately measure blood pressure values made during subsequent pressure-free measurements (squares). In FIG. 4B, the linear fit to the PTT vs. MAP*(P) values, shown by the dashed line 131, does not accurately fit the measurements of PTT vs. MAP. This result is expected based on the variability of the PTT vs. MAP*(P) values, and indicates that this calibration has a relatively low accuracy compared to that made during inflation.

Use of Inflation-Based Oscillometry in the Composite Method

Figures 5A, 5B:
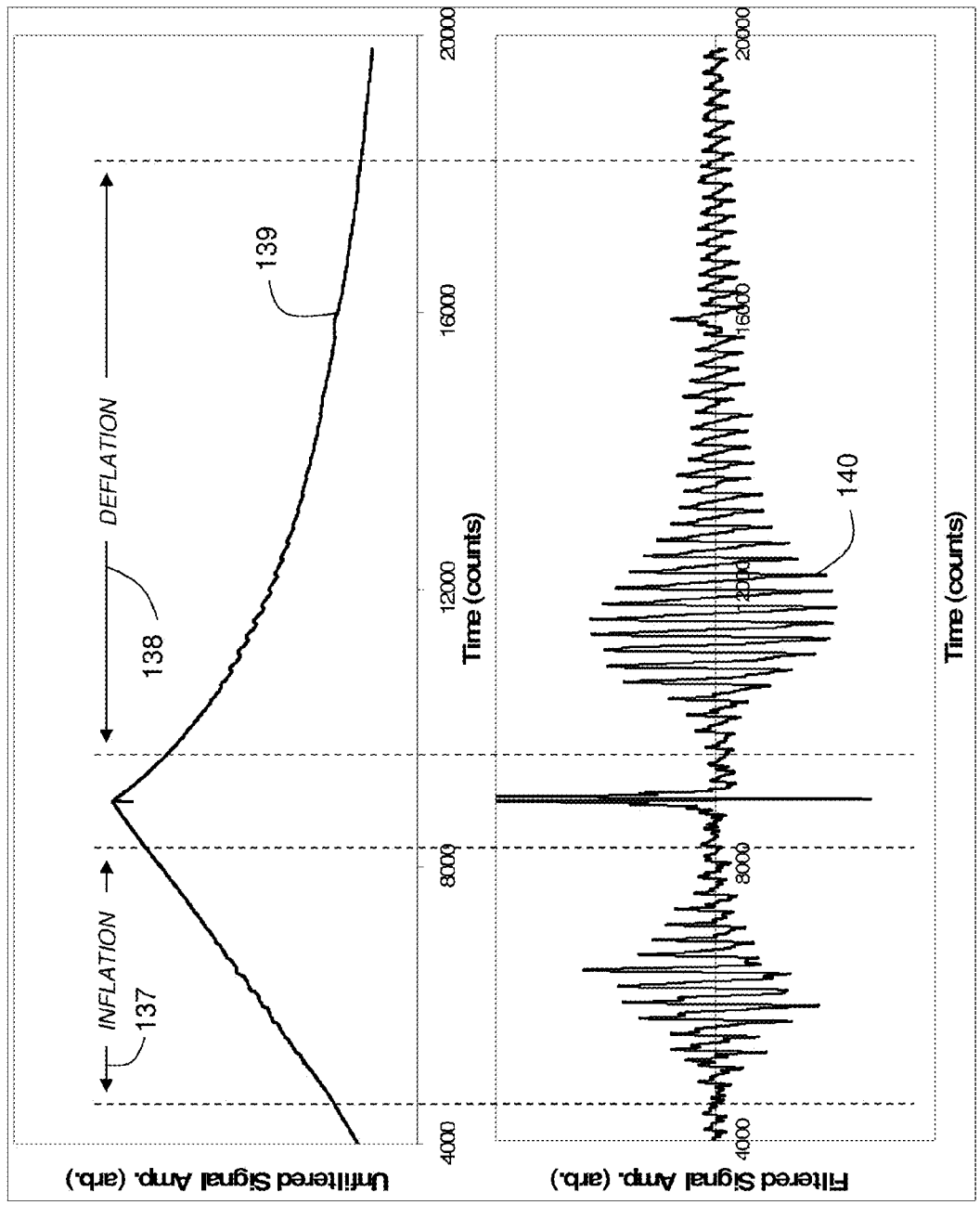
FIG. 5A shows a graph of a time-dependent pressure waveform measured during both inflation and deflation.
FIG. 5B show a graph of a time-dependent pressure waveform measured during both inflation and deflation, and the same waveform after being filtered with a digital bandpass filter.

FIG. 5A illustrates the equivalency between inflation-based and deflation-based oscillometric blood pressure measurements. The top portion of the figure shows an unfiltered pressure waveform 139, measured during the pressure-dependent measurement, which includes periods of both inflation 137 and deflation 138. Pulses associated with the patient's heartbeat couple into a bladder in the cuff during both periods. Following a measurement, the pressure waveform 139 is processed using a 0.5→5.0 Hz digital bandpass filter to remove the slowly varying baseline. As shown in FIG. 5B, filtering results in a time-dependent pressure waveform 140 featuring separate pulse trains measured during both inflation and deflation; the time-dependent amplitudes of each pulse in the train are characterized by a Gaussian envelope. Pressure corresponding to the peak of the Gaussian envelope represents a direct measurement of mean arterial pressure. Diastolic blood pressure, which is measured indirectly, corresponds to a pressure less than mean arterial pressure when the ratio of the envelope to its maximum value is 0.72. This ratio, along with the ratio for systolic blood pressure (typically 0.55), is described in more detail in U.S. Pat. No. 6,719,703, the contents of which are incorporated herein by reference.

As described above, oscillometry is used during the indexing measurement to determine $SYS_{INDEX}$, $DIA_{INDEX}$, and $MAP_{INDEX}$. These values are extracted from a 'processed pressure waveform', shown in FIG. 6, which is determined from a pressure waveform collected during inflation as shown in FIG. 5. The pressure waveform indicates how amplitude of each heartbeat-induced pulse in the time-dependent pressure waveform varies with pressure applied by the cuff. During a measurement, a pressure sensor in the pneumatic system shown in FIG. 24A collects and digitizes the pressure waveform, which is then processed as described below to determine the processed pressure waveform, and ultimately $SYS_{INDEX}$, $DIA_{INDEX}$, and $MAP_{INDEX}$.

A two-stage digital filtering algorithm determines the processed pressure waveform. This involves first filtering the raw pressure waveform with a bandpass filter that, in typical applications, features a second-order infinite impulse response (IIR) function that passes frequencies between 0.5→7.5 Hz. The second-order IIR filter transfer function typically takes the form:

$$H_F(z) = \frac{b_0 z^2 + b_1 z + b_2}{z^2 + a_1 z + a_2} \quad (3)$$

and is implemented as a difference equation, as shown in Equation (4):

$$y[n] = b_0 x[n] + b_1 x[n-1] + b_2 x[n-2] a_1 y[n-1] - a_2 y[n-2] \quad (4)$$

Input to the first stage of the IIR filter is the raw, unprocessed pressure waveform, similar to that shown in FIG. 5A. Processing with the first stage yields the pulse waveform, similar to that shown in FIG. 5B. In order to remove any phase distortion, the IIR filter is executed in both the forward and reverse directions. The reverse filtering step doubles the effective order of the filter, and cancels out any phase distortion introduced by the forward filtering operation. The reverse filtering step is implemented by executing the standard IIR difference equation (i.e. Equation (4)), performing a time-reversal on the outputted data, and then executing the same IIR difference equation. While effective in removing phase distortion, such additional steps require an extra difference computation which cannot be performed in real-time on a stream of data. This, in turn, increases power consumption in the wrist-worn transceiver, and thus shortens battery life.

As the cuff inflates around the patient's arm, perturbations due to patient motion, kinks in the cuff, rapid speed changes in the pump's motor, and other artifacts may affect the pressure waveform. Such perturbations are typically non-physiological, and thus should be removed to minimize their influence on the oscillometric envelope. Their impact can be minimized by a number of different techniques. These include setting certain, noise-containing sections of the pressure waveform equal to zero and removing any data points in the waveform that show a rapid change in value over a relatively short period of time. After the potential artifacts have been removed, the pulse waveform is rectified to prepare for the second filtering operation. Rectification involves transforming the waveform into a new waveform ($P_{RECT}$) that features only positive components. $P_{RECT}$ is calculated from the original pressure waveform ($P_{ORIG}$) using Equation (5), below:

$$P_{RECT}(i) = \begin{cases} -1 \times P_{ORIG}(i) & \text{if } P_{ORIG}(i) < 0 \\ P_{ORIG}(i) & \text{otherwise} \end{cases} \quad (5)$$

Figure 6:
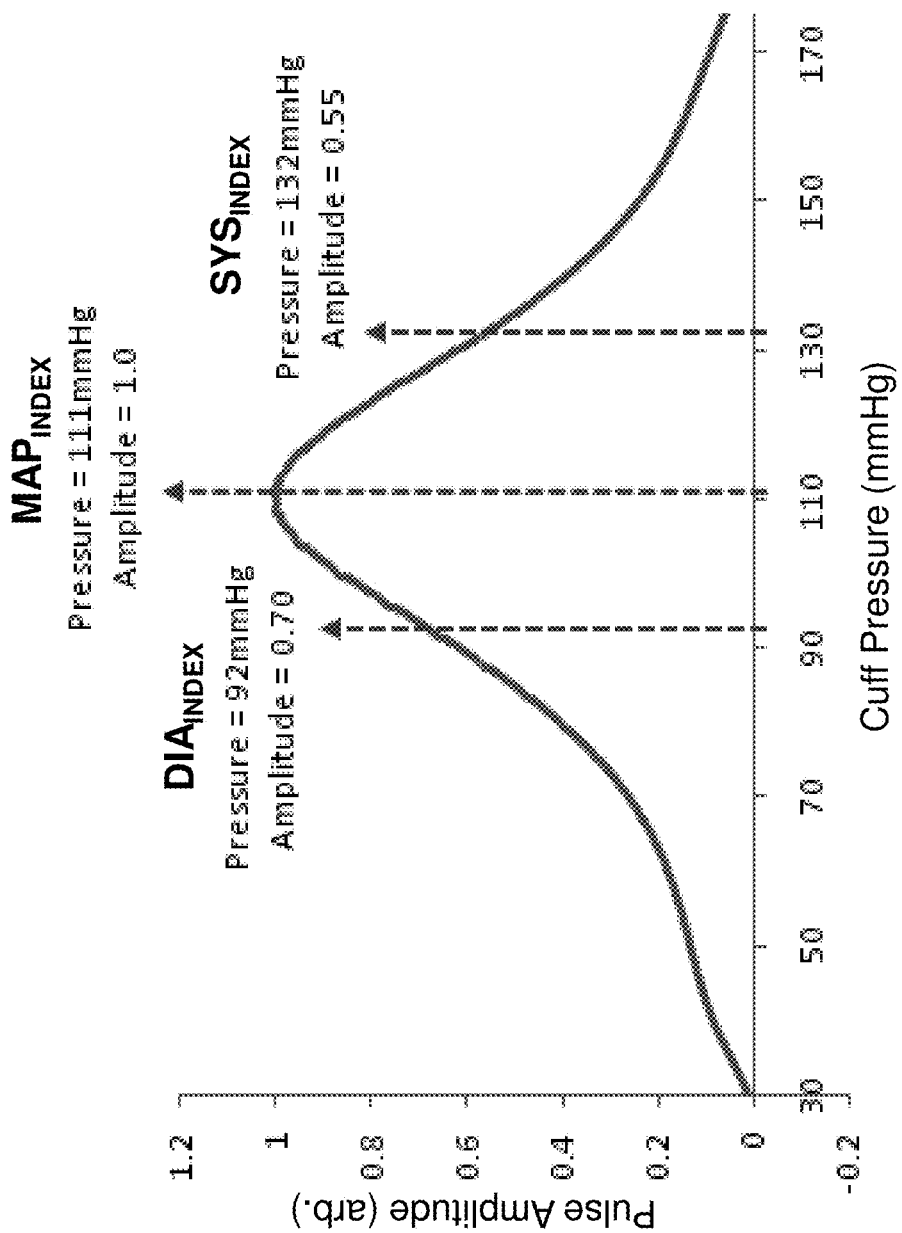
FIG. 6 shows a graph of amplitudes corresponding to heartbeat-induced pulses taken from the inflationary portion of the graph in FIG. 5B and plotted as a function of pressure applied to a patient's brachial artery.

To complete the second phase of the filtering process, the rectified waveform is filtered with a digital low-pass filter based on an IIR filter. The low-pass filter typically only passes components less than 0.2 Hz to yield a smooth, low-frequency envelope indicating the pulse amplitude variation, as shown in FIG. 6. This waveform represents the 'processed pressure waveform', and can then be analyzed with techniques borrowed from oscillometry to determine the patient's 'indexed' blood pressure values, i.e. $SYS_{INDEX}$, $DIA_{INDEX}$, and $MAP_{INDEX}$. Specifically, the peak of the processed pressure waveform corresponds to $MAP_{INDEX}$. This is because, during oscillometry, the maximum amplitude of the heartbeat-induced pulses occurs when the brachial transmural pressure is zero. This takes place when the pressure inside the cuff equals MAP in the brachial artery. Oscillometry thus represents a direct measure of MAP. Both $SYS_{INDEX}$ and $DIA_{INDEX}$ are calculated using an empirical model based on amplitudes of the waveform on both sides of $MAP_{INDEX}$, as indicated in FIG. 6. During an actual measurement, the peak of the processed pressure waveform is determined using standard means, such as calculating a mathematical derivative and determining a positive-to-negative zero-point crossing. $SYS_{INDEX}$ and $DIA_{INDEX}$ are then determined from features of the waveform located, respectively, at higher and lower pressures compared to $MAP_{INDEX}$. Referring again to FIG. 6, $SYS_{INDEX}$, for example, is the pressure corresponding to 0.55 times the peak amplitude on the right-hand (high-pressure) side of the processed pressure waveform. $DIA_{INDEX}$ is the pressure corresponding to 0.70 times the peak amplitude on the left-hand (low pressure) side of the waveform.

The above-described ratios (0.55 and 0.70) corresponding to $SYS_{INDEX}$ and $DIA_{INDEX}$ are typically determined empirically using studies with a large and diverse patient population. They can vary with physiological properties associated with a given patient. For example, the ratios can vary depending on the patient's MAP, shape of the processed waveform, heart rate, biometric data (e.g. gender, height, weight, age), and other factors. A reference that describes the variation of ratios with the shape of the processed pressure waveform is described in the following reference, the contents of which are fully incorporated herein by reference: Amoore et al., 'Effect of the shapes of the pulse amplitude oscillometric envelope and their characteristic ratios on the differences between auscultatory and oscillometric blood pressure measurements', *Blood Pressure Monitoring* 2007;

12:297-305. Once determined, the resultant values for $MAP_{INDEX}$, $SYS_{INDEX}$, and $DIA_{INDEX}$ can be checked for accuracy using a variety of simple tests. For example, $MAP_{INDEX}$ can be compared to the geometric MAP ($MAPG_{GEO}$) determined from $SYS_{INDEX}$ and $DIA_{INDEX}$ using Equation (6), below. This test is based on the inherent relationship between MAP, SYS, and DIA, as described in the following reference, the contents of which are fully incorporated herein by reference: Chemla et al., 'Mean aortic pressure is the geometric mean of systolic and diastolic pressure in resting humans', J Appl Physiol 2005; 99:2278-2284.

$$|MAP_{DIFF}|>DIFF_{MAX}, \text{where } MAP_{DIFF}= (MAP_{INDEX}-MAP_{GEO}) \quad (6)$$

In Equation (6) $MAP_{GEO}$ is determined from the following equation:

$$MAP_{GEO}=\sqrt{(SYS_{INDEX} \times DIA_{INDEX})} \quad (7)$$

In embodiments, for example, $DIFF_{MAX}$ is equal to 13 mmHg. This means a measurement is rejected if the difference between $MAP_{INDEX}$ and $MAP_{GEO}$ is greater or less than 13 mmHg. Such a situation would occur, for example, if the processed pressure waveform was distorted by a motion-related artifact that occurred during the oscillometric measurement. When an oscillometric measurement is rejected, a NULL value is returned, and the body-worn monitor instructs the pneumatic system to re-inflate the cuff, and the measurement is repeated.

Once $MAP_{INDEX}$, $SYS_{INDEX}$, and $DIA_{INDEX}$ are determined, the systolic and diastolic ratios ($R_{SYS}$ and $R_{DIA}$) are calculated as described below in Equation (8):

$$R_{SYS}=SYS_{INDEX}/MAP_{INDEX}$$

$$R_{DIA}=DIA_{INDEX}/MAP_{INDEX} \quad (8)$$

These ratios may vary in a dynamic fashion according to other physiological parameters determined during a measurement, particularly heart rate. Such variation is described in the above-referenced journal article, entitled Chemla et al., 'Mean aortic pressure is the geometric mean of systolic and diastolic pressure in resting humans', J Appl Physiol 2005; 99:2278-2284, the contents of which have been previously incorporated by reference. For example, Equation (9), below, indicates how these ratios may vary with heart rate:

$$R_{SYS}=a \times HR \times SYS_{INDEX}/MAP_{INDEX}$$

$$R_{DIA}=b \times HR \times DIA_{INDEX}/MAP_{INDEX} \quad (9)$$

In Equation (9), the coefficients a and b are determined empirically, typically using studies on either humans or animals. For these studies blood pressure and heart rate data are typically collected with a diverse group of patients undergoing a range of physiological conditions, and then analyzed. Note that the ratios shown in Equation (9) will only exhibit dynamic behavior if the patient's heart rate is variable.

As described above, the Composite Method can also include an intermediate pressure-dependent indexing measurement that determines systolic, diastolic, and means arterial pressures using an abbreviated applied pressure. In this case, to find systolic blood pressure, the algorithm can detect the amplitude of each pulse in the PPG waveform, and fit them to a variety of mathematical models to 'predict' and extrapolate exactly where the amplitude decreases to zero. For example, the algorithm can fit the last eight data points in FIG. 4B to a linear function. In this case knowledge of the patient's heart rate (e.g. frequency and rhythm), as determined from the ECG waveform, can enhance the accuracy of the prediction and provide a confidence indicator of the metric. The algorithm may take a mathematical derivative of the PPG waveform to eliminate any affects of the waveform's baseline. The above-described algorithms may then be used to predict disappearance of the pulse and thus the onset of systolic blood pressure.

During the intermediate pressure-dependent measurement, pressure is typically applied until just after mean arterial pressure is calculated as described above, and then terminated. At this point, the amplitude of the PPG waveform is typically in decline, and can be fit with the linear function to predict systolic blood pressure. Both systolic and mean arterial pressures are then used to determine diastolic pressure, as described above. The intermediate pressure-dependent measurement is typically performed, for example, every 4 hours in place of the regular pressure-dependent measurement.

Measuring PTT and Determining cNIBP with the Composite Method

Figure 7B:
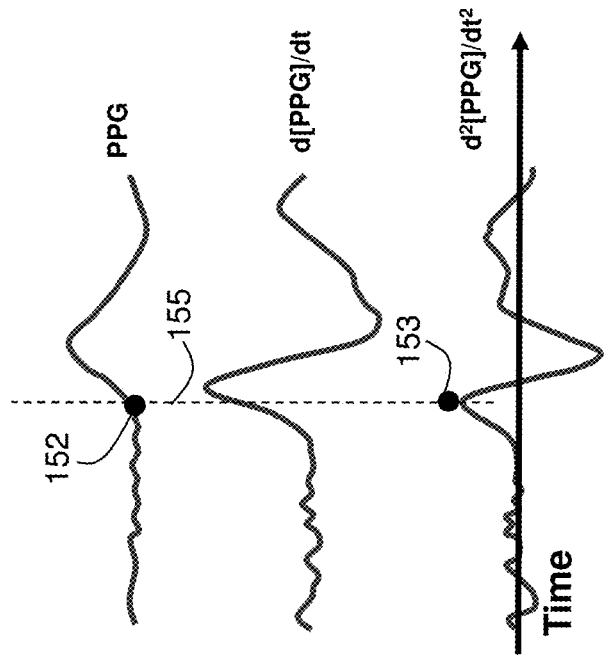
FIG. 7B shows a graph of the time-dependent PPG waveform of FIG. 7A (top trace), the first derivative of the waveform (middle trace), and the second derivative of the PPG waveform (bottom trace)
Figure 7A:
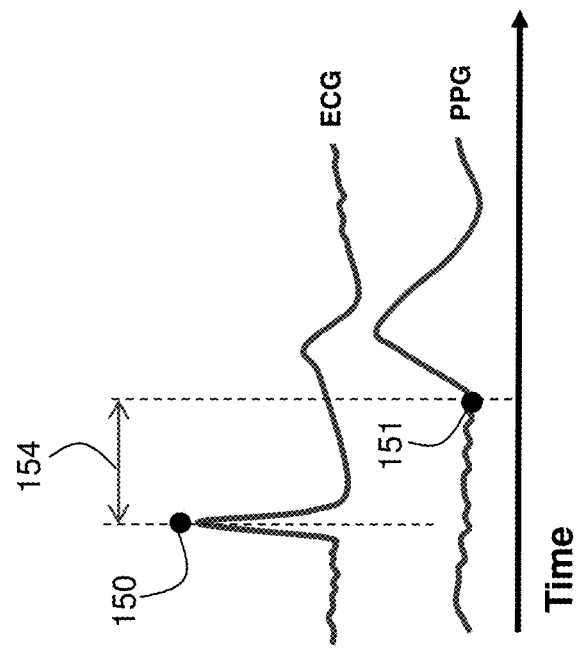
FIG. 7A shows a graph of time-dependent ECG and PPG waveforms and markers associated with these waveforms used to determine PTT.

Following indexing, cNIBP is determined on a beat-by-beat basis from PTT, which as indicated by the arrow 154 in FIG. 7A is determined from the time difference between features in the ECG and PPG waveforms. Specifically, PTT separates a sharply peaked QRS complex in the ECG waveform, indicated in the figure by the black circle 150, from the base of the PPG waveform, shown by the black circle 151. PTT typically varies inversely with blood pressure, i.e. a decrease in PTT indicates an increase in blood pressure. In theory, PTT is affected by blood pressure and a variety of other factors, such as arterial compliance, arterial size, vascular resistance, PEP, and LVET. For this reason, PTT, taken by itself, only indicates relative changes in blood pressure. But when combined with the above-mentioned indexing process, which estimates absolute blood pressure values and 'calibrates' for factors that affect PTT but not necessarily blood pressure, PTT can accurately monitor cNIBP. As described above, during a measurement the body-worn monitor measures PTT corresponding to every heartbeat for a given time period, typically lying between 20-60 seconds. During this time period, specific PTT values may be filtered out to remove erroneous values affected by artifacts, such as motion. For example, both average and standard deviation values can be calculated for a set of PTT values measured during the time period. The total number of PTT values will, of course, depend on the heart rate, and is typically between 15 and 60 for a 30-second measurement period. Values that differ from the average by more than one standard deviation can be assumed to be artificial, and thus removed from the calculation. At this point an average PTT value is then recalculated for the time period and used for the subsequent cNIBP calculation. Similar statistical processing techniques, such as those using numerical fitting, processing of Gaussian distributions, or digital filtering, can also be used to exclude PTT values estimated to be erroneous. Statistics are typically calculated for individual time periods. Alternatively, they may be calculated on a 'rolling basis' in which the time period is kept relatively large, but is sequentially updated, e.g., each second. This approach has the advantage that it can yield a 'fresh' blood pressure value at a relatively high frequency.

Referring again to FIG. 7A, PTT is typically calculated from the foot or 'onset' of the PPG waveform, indicated by the black circle 151, which indicates an arrival of the pressure pulse. Physically, the onset point 151 represents beginning of a volumetric increase in vasculature that lies underneath the thumb-worn sensor (294) shown in FIG. 24A. A pressure pulse launched by the patient's beating heart propagates along their vasculature, driving blood into it and causing a temporary expansion upon its arrival. The expansion increases optical absorption according to the Beer-Lambert law. Radiation that passes through the expanding vasculature is detected by a photodetector, resulting in a time-dependent PPG. Technically, the waveform shown in FIG. 7A is an inverted version of the 'true' PPG, as the increase in optical absorption reduces the amount of radiation and resulting signal detected by the photodetector within the thumb-worn sensor.

Alternatively, PTT can be calculated from other regions of the waveform, such as a point along its rising edge or its peak. Timing associated with these regions, however, may be affected by properties of the underlying vasculature (such as elasticity) that are decoupled from blood pressure. For this reason they are less desirable than the waveform's onset. In embodiments, however, they may be used to augment calculation of PTT. For example, as shown by the middle trace of FIG. 7B, the first derivative of the PPG yields a well-defined peak indicating the maximum slope of the PPG that can easily be detected with a computer algorithm. For unusually noisy PPGs, this fiducial marker may be used to help locate the PPG's onset, or may be processed with the onset to generate an 'average' PTT value for the waveform. Other features of the waveform, such as its maximum value, may also be processed in a similar manner.

In other embodiments, multiple PPGs measured during a SpO2 measurement may be processed to generate a single PTT. Such a measurement is described in the following co-pending patent application, the contents of which are fully incorporated herein by reference: 'BODY-WORN PULSE OXIMETER' (U.S. Ser. No. 12/559,403; filed Sep. 14, 2009). As described in this reference, during a typical SpO02 measurement PPGs are measured with both red (~660 nm) and infrared (~905 nm) wavelengths. These PPGs have similar features, but may be affected by motion-related noise, as well as other artifacts such as ambient light, in different ways. The onset of each PPG can thus be independently detected, and then averaged together to generate a single PTT. Other techniques for processing multiple PPGs to determine a single PTT are described below, particularly with reference to FIGS. 15-17.

FIG. 7B shows one method for determining the onset of a PPG waveform, indicated in the top portion of the figure by the black circle 152. Before processing, the PPG waveform is typically filtered with a digital finite impulse response (FIR) filter, which removes high-frequency noise from the waveform prior to processing. Such noise is typically due to electrical or mechanical sources. Removing it is critical for effective signal processing, as it is amplified after taking a numerical derivative. This reduces a signal-to-noise ratio of the derivatized waveform, which in turn may lead to erroneous measurements. The first derivative of the PPG waveform peaks at a point corresponding to the maximum rise time of the unprocessed PPG waveform. This point, shown in the middle trace of FIG. 7B, typically follows the onset point by 20-100 ms. As shown as the bottom trace in the figure, the second derivative of the waveform peaks at a point corresponding to the onset. This is indicated in the figure by the black circle 153, and correlates with the PPG onset as indicated by the dashed line 155. Such a peak is characterized by a well-defined positive-to-negative slope change, and is relatively easy to detect with a standard computer algorithm. Once detected, this value is processed along with the ECG QRS to determine PTT.

Once determined, PTT is used along with blood pressures determined during indexing with inflation-based oscillometry ($MAP_{INDEX}$, $SYS_{INDEX}$, and $DIA_{INDEX}$) and a patient-specific slope ($m_{cNIBP}$) to determine a MAP component of cNIBP ($MAP_{cNIBP}$). Equation (10), below, shows the relationship between these parameters:

$$MAP_{cNIBP} = (m_{cNIBP} \times PTT) - (m_{cNIBP} \times PTT_{INDEX}) + MAP_{INDEX} \quad (10)$$

where $PTT_{INDEX}$ is the PTT value determined at the start of the indexing process. $SYS_{cNIBP}$ and $DIA_{cNIBP}$ are then determined from $MAP_{cNIBP}$ for each heartbeat using the relationships described in Equation (11), below:

$$SYS_{cNIBP} = MAP_{cNIBP} \times R_{SYS}$$

$$DIA_{cNIBP} = MAP_{cNIBP} \times R_{DIA} \quad (11)$$

where $R_{SYS}$ and $R_{DIA}$ are described above in Equation (8) and, optionally, Equation (9).

In other embodiments, the blood pressure ratios shown in Equation (11) can be adjusted depending on other signals measured from the patient, such shapes associated with the PPG and ECG waveforms. For example, a relationship between the PPG waveform shape and SYS, DIA, and MAP that can be used in this embodiment is described in U.S. Pat. No. 5,269,310, the contents of which are incorporated herein by reference. In other embodiments, unique patient-specific slopes and y-intercepts relating SYS, DIA, and MAP to PTT, similar to that shown for $MAP_{cNIBP}$ in Equation (10), can be determined beforehand and used to independently calculate these blood pressures. In still other embodiments, 'default' slopes calculated beforehand from large groups of patients can be used in place of the patient-specific slopes. A default slope would be used, for example, if it were difficult to determine a patient-specific slope as described above because of a motion-related artifact or a problem associated with the pneumatic system.

Implementation of the Composite Method

Figure 8:
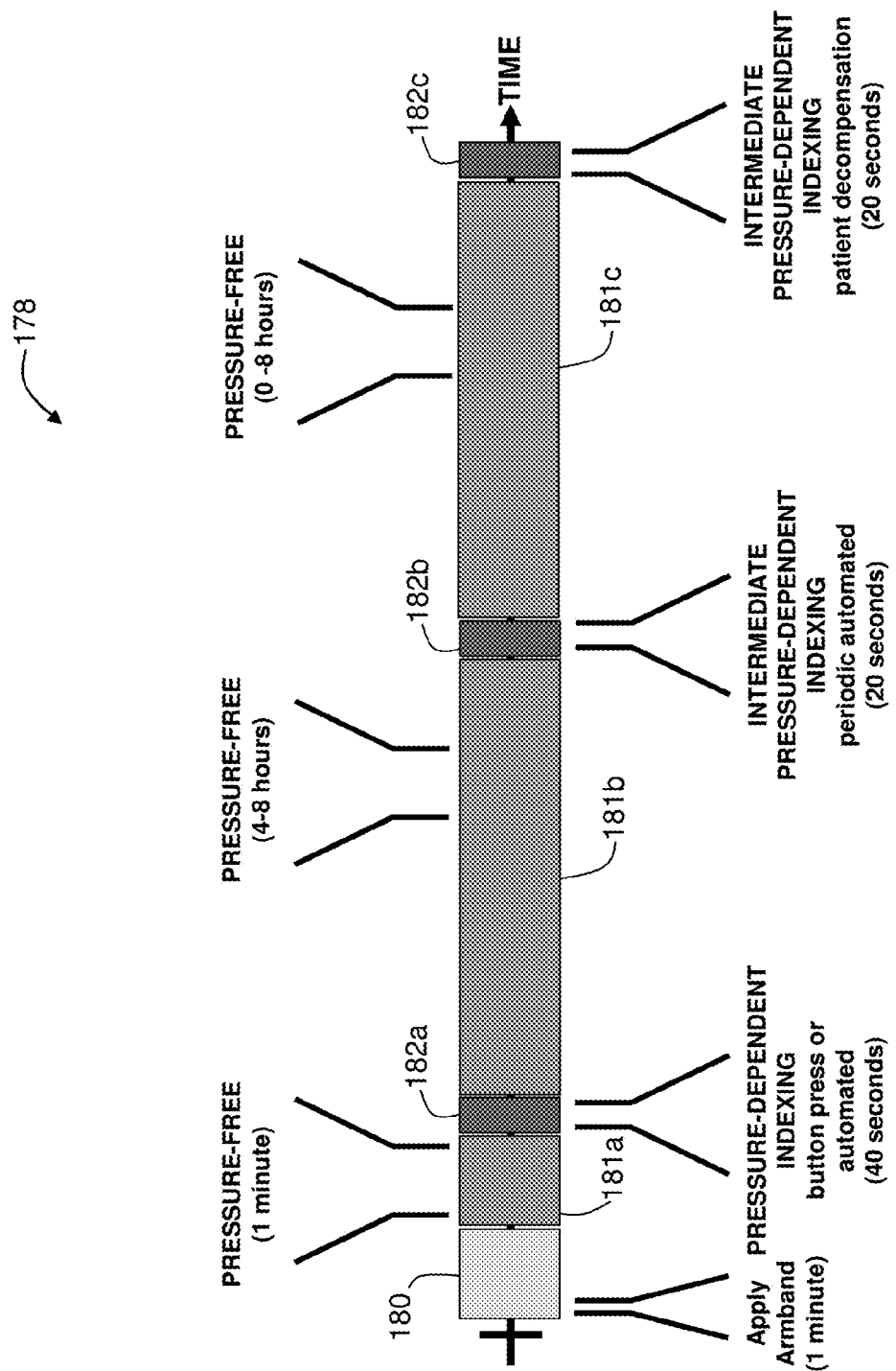
FIG. 8 is a schematic drawing showing a sequence of pressure-dependent and pressure-free measurements made during the Composite Method.

FIG. 8 shows one possible sequence 178 of the Composite Method's pressure-dependent (steps 182a), pressure-free (steps 181a, 181b, 181c), and intermediate pressure-dependent (steps 182b, 182c) measurements for a patient undergoing an extended hospital stay. During the stay, a medical professional applies the body-worn monitor, optical sensor, and chest electrodes to the patient (step 180). This takes about one minute. The medical professional may also collect biometric information from the patient, such as their age, weight, height, gender, ethnicity, and whether they are on blood pressure medications, and enter these into the monitor using a graphical user interface and touch panel. This information is then communicated wirelessly to the remote monitor. Going forward, a microprocessor within the body-worn monitor's electronics module first initiates a pressure-free measurement (step 181a) for about one minute, wherein the body-worn monitor collects PPG and ECG waveforms from the patient, determines their heart rate and PTT, and can estimate their blood pressure. In the absence of an absolute blood pressure measurement from the Composite Method's pressure-dependent measurement, the microprocessor may use PTT and the patient's biometric information to estimate blood pressure, as is described in the following co-pending patent application, the contents of which have been previously incorporated herein by reference: DEVICE AND METHOD FOR DETERMINING BLOOD PRESSURE USING 'HYBRID' PULSE TRANSIT TIME MEASUREMENT (U.S. Ser. No. 60/943,464; filed Jun. 12, 2007); and, VITAL SIGN MONITOR FOR CUFFLESSLY MEASURING BLOOD PRESSURE USING A PULSE TRANSIT TIME CORRECTED FOR VASCULAR INDEX (U.S. Ser. No. 60/943,523; filed Jun. 12, 2007). This process typically determines systolic and diastolic blood pressure with an accuracy of about ±10-15 mmHg.

The initial, approximate value for the patient's blood pressure and heart rate determined during the first pressure-free measurement (step 181a) can then be used to set certain parameters during the following first pressure-dependent indexing measurement (step 182a). Knowledge of these parameters may ultimately increase the accuracy of the first pressure-dependent measurement (step 182a). Such parameters, for example, may include inflation time and rate, fitting parameters for determining the time-dependent increase in PTT and the time-dependent decrease in PPG waveform amplitude during the pressure-dependent measurement. Of particular importance is an accurate value of the patient's heart rate determined during the first pressure-free measurement (step 181a). Since both PTT and amplitude can only be measured from a pulse induced by a heartbeat, the algorithm can process heart rate and use it in the fitting process to accurately determine the pressure at which the PPG waveform amplitude crosses zero.

Using parameters such as heart rate and initial estimated blood pressure, the first pressure-dependent indexing measurement (step 182a) determines a relationship between PTT and blood pressure as described above. This measurement takes about 40 seconds, and may occur automatically (e.g., after about 1 minute), or may be driven by the medical professional (e.g., through a button press). The microprocessor then uses this relationship and a measured value of PTT to determine blood pressure during the following pressure-free measurement (step 181b). This measurement step typically proceeds for a well-defined period of time (e.g., 4-8 hours), during which it continuously determines blood pressure. Typically, to conserve battery life, the body-worn monitor averages PTT values over a 10-20 second period, and makes one blood pressure measurement every 3-5 minutes.

The microprocessor may also perform a pre-programmed or automated intermediate pressure-dependent measurement (step 182b) to correct any drift in the blood pressure measurement. As described above, this step involves only partial inflation of the bladder within the cuff, during which the microprocessor fits the pressure-dependent decrease in the amplitude of pulses in the PPG waveform to a linear model. This measurement takes less time than the first pressure-dependent measurement (step 182a), and accurately determines blood pressure values that are used going forward in a second pressure-free measurement (step 181c). As before, this measurement typically continues for a well-defined period of time. At a later time, if the patient experiences a sudden change in other vital signs (e.g., respiratory rate, heart rate, body temperature), the microprocessor may analyze this condition and initiate another pressure-dependent blood pressure measurement (step 182c) to most accurately determine cNIBP.

Correlation Between cNIBP Measurements Made with the Composite Method and a Femoral A-Line cNIBP measurements made according to the Composite Method correlate particularly well to blood pressure continuously measured from a patient's femoral artery using an arterial catheter, or 'A-line'. Correlating cNIBP measurements to this reference standard represents an improvement over many previous studies that relate PTT to blood pressure measured with an A-line inserted a patient's radial artery, a location that is commonly used in hospital settings, such as the ICU. Such studies are described, for example, in the following references, the contents of which are incorporated herein by reference: Payne et al., 'Pulse transit time measured from the ECG: an unreliable marker of beat-to-beat blood pressure', *J Appl Physiol* 2006; 100:136-141. One reason for poor agreement between blood pressure measured with PTT and a radial A-line involves a phenomenon called 'pulse pressure amplification' wherein a patient's blood pressure gradually increases along their arterial tree as the diameter of the artery supporting the pressure is decreased, as described in the following reference, the contents of which are fully incorporated herein by reference: Verbeke et al., 'Non-invasive assessment of local pulse pressure: importance of brachial to radial pressure amplification', *Hypertension* 2005; 46:244-248. To summarize, gradual tapering that commonly occurs from the brachial to radial arteries can have little effect on DIA or MAP, but can increase pulse pressure (defined as SYS-DIA) by as much as 10 mmHg or more. For the measurement described herein, this means blood pressure measured at the radial artery is typically higher than that measured at the brachial artery. And this phenomenon can reduce correlation between blood pressure measured using the Composite Method and a radial A-line, as the Composite Method is calibrated using an indexing measurement made at the patient's brachial artery. In contrast, blood pressure at the femoral artery is typically similar to that measured at the brachial artery. The following references, the contents of which are fully incorporated herein by reference, describe the strong correlations between blood pressures measured at these different sites: Park et al., 'Direct blood pressure measurements in brachial and femoral arteries in children', *Circulation* 1970; XLI:2311-237; and Pascarelli et al., 'Comparison of leg and arm blood pressures in aortic insufficiency: an appraisal of Hill's Sign', *Brit Med J* 1965; 2:73-75. Without being bound to any theory, the strong correlation between brachial and femoral pressure may occur because both arteries are large, close to the patient's heart, and support pressures indicative of the patient's core. The relatively large diameters of these arteries may additionally minimize the influence of the arterial wall on the internal pressure. In contrast, the radial artery is a significantly smaller artery with a relatively high surface-to-volume ratio, which tends to increase blood pressure. This is one reason, for example, that SYS measured at a patient's extremities (using e.g. a finger cuff) is typically higher than their core blood pressure.

Figure 9:
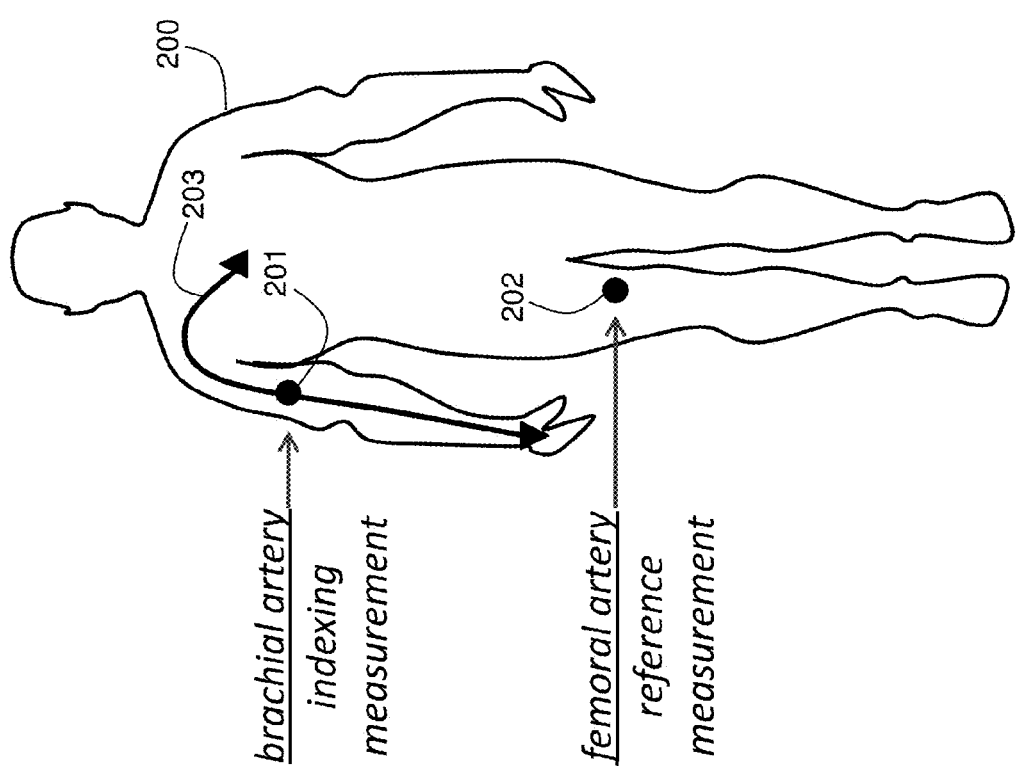
FIG. 9 is a schematic drawing showing how, during a clinical trial, an indexing measurement is made from the patient's brachial artery, and a reference measurement using an A-line is made from the patient's femoral artery.

FIG. 9 shows a graphic that this indicates this effect. In the figure, a patient 200 undergoing a cNIBP measurement has an indexing measurement performed at their brachial artery, as indicated by the black circle 201. As described above, the indexing measurement yields oscillometric blood pressures and a patient-specific relationship between PTT and blood pressure. These parameters are specific to the brachial artery, but also agree well with those determined at other large arteries, such as the femoral arteries. PTT indicates a transit time describing the delay associated with a pressure pulse launched by the patient's heartbeat and arriving at the optical sensor, which is typically located on their thumb. The pathway associated with the transit time is shown by the line 203 in the figure. During a correlation study, a reference measurement is typically made using an A-line inserted into the patient's femoral artery, as shown by the black circle 202. Correlation between these two measurements is typically very good, presumably because the large nature of both the femoral and brachial arteries limits the influence of pulse pressure amplification, particularly on SYS values.

In some cases, however, instantaneous blood pressure measured at both the femoral and brachial arteries do not agree. According to the above-described references (particularly Pascarelli et al.), differences between these pressures may be as large as 20 mmHg, and typically result from cardiac problems such as blockages or 'aortic insufficiencies'. Differences tend to be larger for unhealthy patients. They typically affect the average difference, or bias, between the cNIBP measurement described herein and the reference A-line measurement, but have little effect on the correlation between these two measurements. If a blood pressure study with a large number of patients is performed, differences between femoral and brachial blood pressures may also contribute to an inter-subject (i.e. 'between subject) error, typically characterized by a standard deviation. Such errors can be compensated for during the study with a calibration approach involving measuring brachial blood pressure with a reference technique, such as manual auscultation, and using this value to estimate the patient's inherent brachial-femoral blood pressure difference. In this case a calibration measurement indicates if disagreement between cNIBP and femoral A-line measurements are caused by device-to-device measurement differences, or human physiology.

Clinical Results

Figure 10:
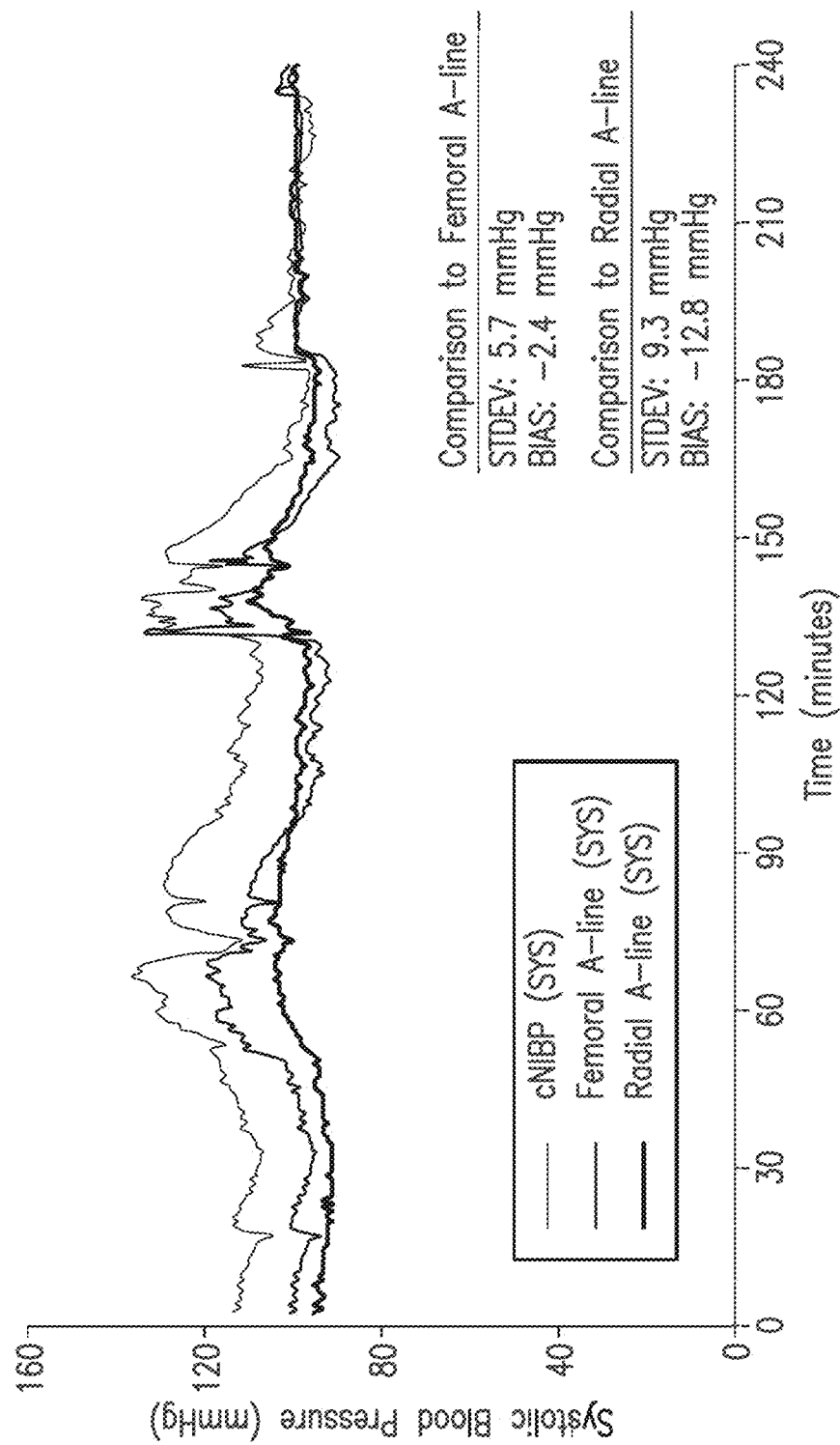
FIG. 10 shows a graph of time-dependent SYS values measured with the Composite Method (black trace), a femoral A-line (dark gray trace), and a radial A-line (light gray trace)

FIG. 10 shows a typical, time-dependent cNIBP measurement according to the Composite Method, and how this yields a SYS value that correlates better with blood pressure measured at the femoral artery compared to the radial artery. For this study, each of the above-mentioned blood pressures (cNIBP, femoral, radial) were measured simultaneously. All measurements were performed in the ICU of a hospital based in San Diego, Calif. Both femoral and radial pressures were measured every second with in-dwelling A-line catheters connected to a conventional vital sign monitor (Philips Intellivue). cNIBP was simultaneously measured and averaged over a 40-second period with a device similar to that shown in FIG. 24. Data from the Philips Intellivue monitor was sent through a serial connection to a specialized data-acquisition computer running a custom software application, while data from the cNIBP measurement was sent through a wireless connection (using Bluetooth) to the same computer. Once collected by the data-acquisition computer, blood pressure values from the A-lines were averaged over an identical 40-second period, and then compared to the cNIBP data. All data for these experiments were collected over a 4-hour period with a single indexing measurement performed at the beginning of the study.

As shown in FIG. 10, cNIBP measurements (black trace) agree fairly well with corresponding measurements from the femoral A-line (dark gray trace) over the entire 4-hour period, with both the STDEV (5.7 mmHg) and BIAS (−2.4 mmHg) between paired values of these measurements falling well below the FDA's standards for blood pressure monitoring devices (STDEV<8 mmHg; BIAS<+/−5 mmHg). These standards are described in detail in the AAMI SP-10:2002, a standards document that outlines requirements for blood pressure monitoring devices. As described above, particularly with reference to FIG. 9, the cNIBP measurement is indexed with an oscillometric measurement made at the subject's brachial artery, a relatively large vessel that, like the femoral artery, supports a pressure that is representative of core blood pressure. Larger arteries near the patient's core, unlike smaller arteries at the extremities, typically do not facilitate artificially elevated blood pressures due to pulse pressure amplification. Blood pressure measured at the subject's relatively small radial artery (light gray trace) is elevated compared to both cNIBP and femoral blood pressures. Additionally, blood pressure at the radial artery tends to be relatively volatile compared to the other blood pressures. Without being bound to any theory, this too may also be due to pulse pressure amplification. Correlation between radial blood pressure and cNIBP is notably worse than that between cNIBP and femoral blood pressure, with both STDEV (9.3 mmHg) and BIAS (−12.8 mmHg) for the paired values falling outside of the FDA's guidelines. Data similar to that shown in FIG. 10 was collected from 23 subjects in a recent study using the device and method according to the invention.

Figure 11:
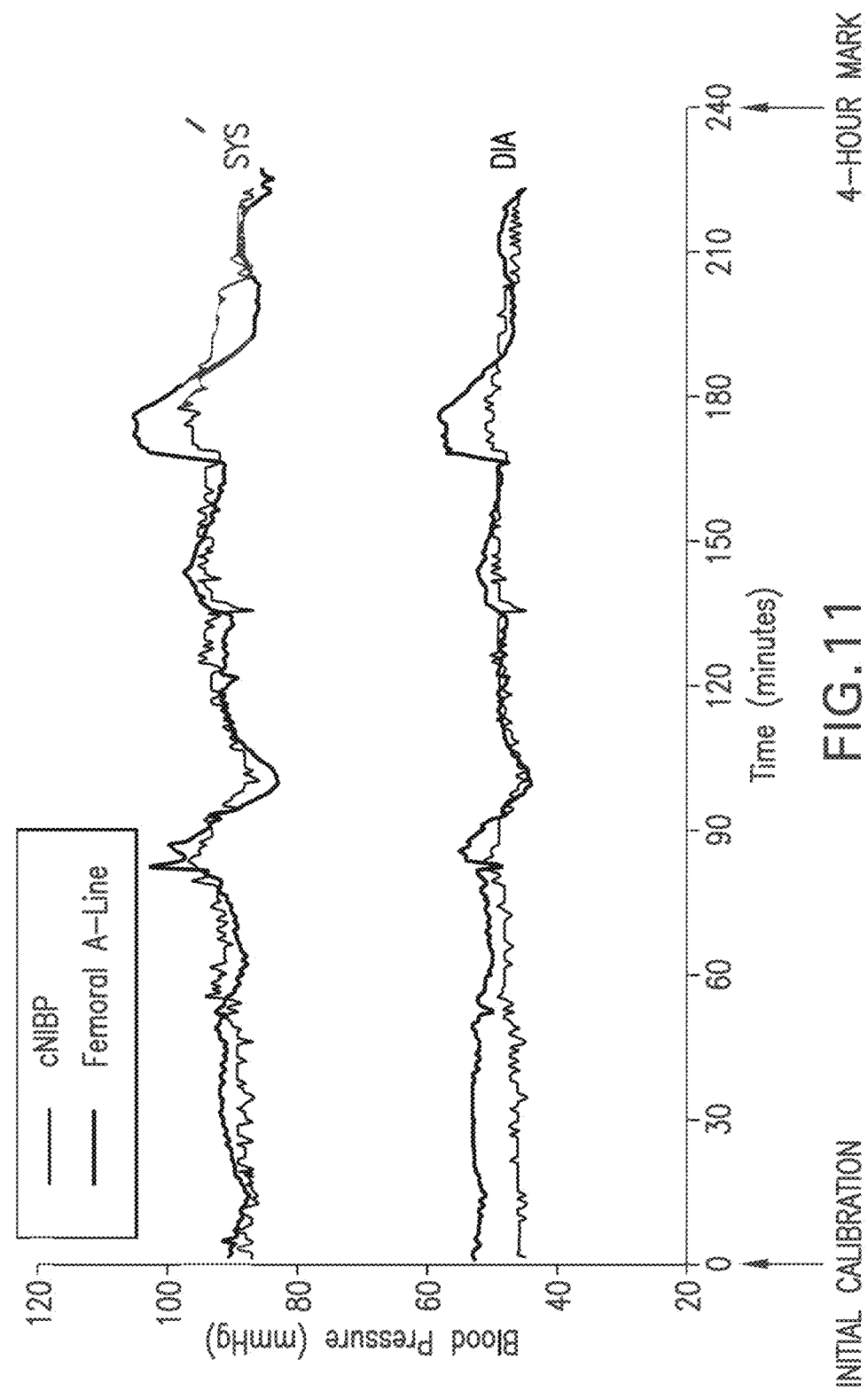
FIG. 11 shows a graph of time-dependent SYS and DIA values measured with the Composite Method (gray trace) and SYS and DIA measured with a femoral A-line.
Figure 12:
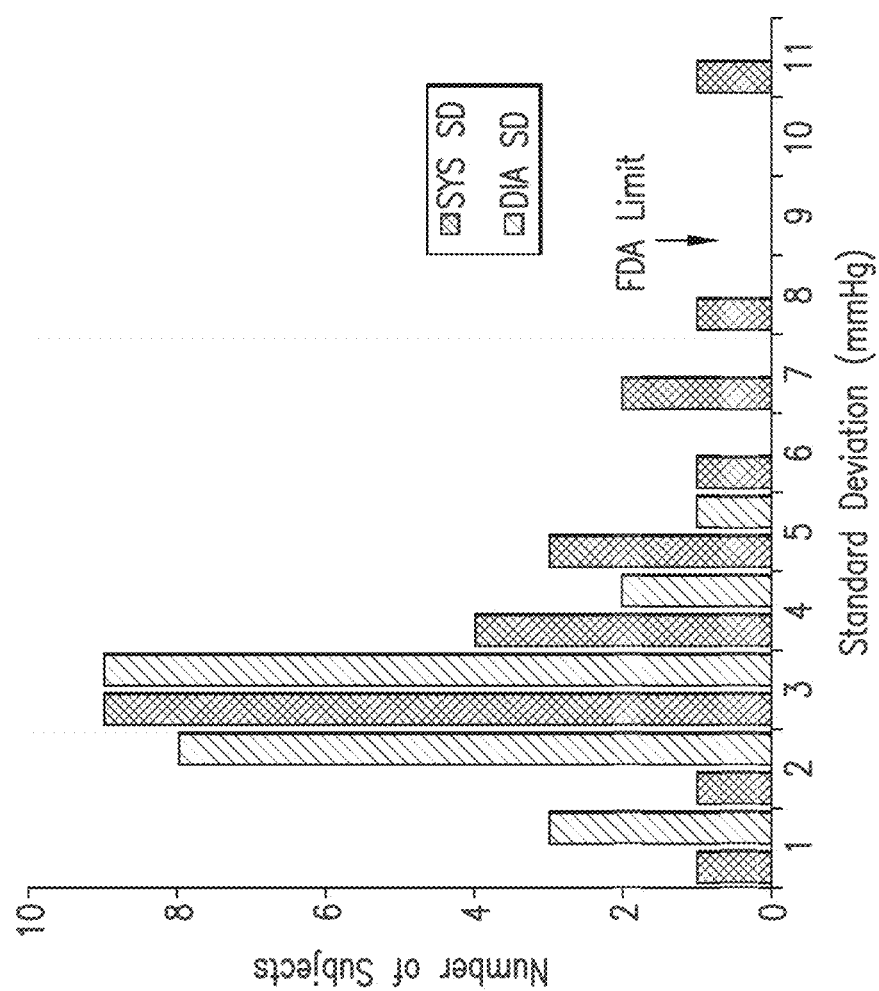
FIG. 12 shows a graph of a histogram of standard deviation values for SYS (dark bars) and DIA (light bars) measured during a 23-subject clinical trial.

FIG. 11 shows typical correlation between both SYS and DIA measured with the Composite Method and a femoral A-line. Data were collected in the same manner described above. Blood pressure was measured over a 4-hour period with only a single indexing measurement performed at the beginning of the study. cNIBP measurements for both SYS and DIA in FIG. 11, like that described above in FIG. 10, correlate well with pressures measured at the femoral artery, and comfortably meet the guidelines required by the FDA. FIG. 12, for example, shows blood pressure correlations (shown as standard deviation) from a cohort of 23 subjects measured in two different ICUs using both the Composite Method and a femoral A-line. All subjects were measured under essentially identical conditions to those described above. The figure shows a histogram that graphs standard deviation values between the two measurements for both SYS (dark gray bars) and DIA (light gray bars). The histogram indicates that, for all measurements collected from 23 subjects, only a single measurement (for SYS) falls outside the FDA's guidelines of 8 mmHg for STDEV. All other measurements are comfortably within this limit, and as expected show Gaussian-type distributions, with the distributions peaked near 3 and 4 mmHg for, respectively, SYS and DIA.

Figure 13:
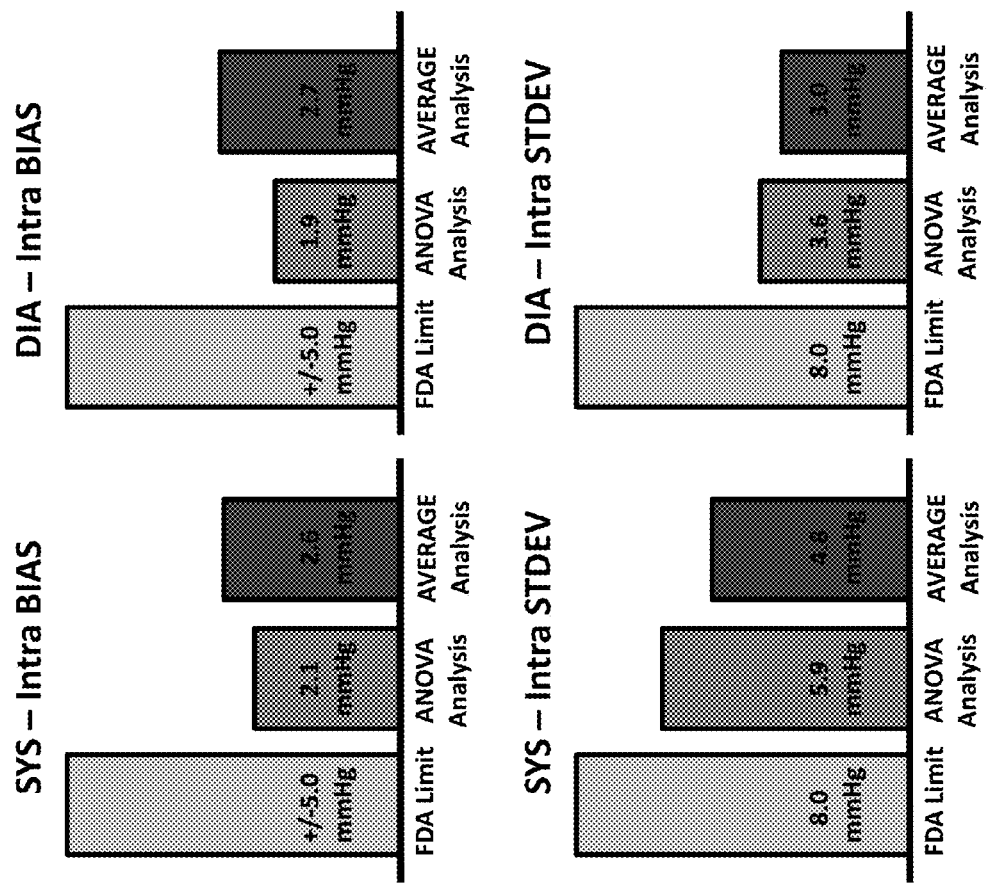
FIG. 13 shows a bar graph of FDA standard values and statistics from the 23-subject study calculated using an ANOVA and AVERAGE methodologies for, respectively, intra-subject BIAS and STDEV for SYS (upper and lower left-hand corners); and intra-subject BIAS and STDEV for DIA (upper and lower right-hand corners)

FIG. 13 shows the collective, intra-subject statistics determined for all 23 subjects for the above-described study. Statistics were determined using two independent techniques. The first technique, called 'analysis of variance' or 'ANOVA', tests statistical variance for a set of repeated measures, like those used in the ICU study. ANOVA models for STDEV and BIAS are commonly used for analysis of data collected in clinical trials, like the one described herein. The second technique shown in FIG. 13 simply calculates the STDEV and BIAS for each subject in the study over the 4-hour measurement period, and then calculates the average of each of these parameters for the group. In general, this 'AVERAGE' analysis is less formal than an ANOVA analysis; it is used herein simply to provide a secondary analysis of the data.

As shown in FIG. 13, for the 23 subjects measured in this study, the intra-subject cNIBP measurements analyzed with both ANOVA and the AVERAGE analysis comfortably meet the FDA's requirements for both intra-subject BIAS and STDEV. For SYS, the intra-subject BIAS was calculated at 2.1 and 2.6 mmHg using, respectively, the ANOVA and AVERAGE analyses. Intra-subject STDEVs for SYS were calculated as 5.9 and 4.8 mmHg using the two techniques. For DIA, the intra-subject BIAS was calculated at 1.9 and 2.7 mmHg using, respectively, the ANOVA and AVERAGE analyses. Intra-subject STDEVs for DIA were calculated as 3.6 and 3.0 mmHg using the two techniques. In all cases, these statistics comfortably meet the FDA's guidelines for BIAS (<+/−5 mmHg) and STDEV (<8 mmHg), as outlined in the above-referenced AAMI SP-10:2002 reference standard.

FIG. 14 shows a table describing drift calculated for the 4-hour measurement period for 22 of the above-mentioned subjects (one subject was excluded because their measurement period was less than 4 hours). Additionally, a follow-on study with 6 subjects investigated drift over an 8-hour measurement period. For this study, a single indexing measurement was performed at the beginning of the measurement, and all subsequent measurements made over the 8-hour period were based exclusively on PTT. In both cases, drift was calculated using a linear regression technique included in a SAS Statistical Analysis Software Package. More specifically, drift was estimated in a repeated-measures mixed-effects general linear model using the 'PROC MIXED' model in SAS. This model includes a 'fixed time effect' model to estimate the drift. As shown in the table, drift over the 4-hour period is relatively small (−0.07 and −0.01 mmHg/hour for, respectively, SYS and DIA), essentially within the error of the cNIBP measurement, and clinically insignificant. Drift for the 8-hour measurement period (−0.4 and -0.3 for, respectively, SYS and DIA) is slightly larger, although still within the error of the cNIBP measurement and likely clinically insignificant.

Drift is an important parameter for characterizing the cNIBP measurement, as it essentially indicates how frequently the Composite Method must be indexed. Drift is generally attributed to a change (either gradual or rapid) in the subject's cardiovascular properties that builds in after an indexing measurement. Such a change, for example, may be attributed to a change in vascular compliance, tone, pre-injection period (PEP), left ventricular ejection time (LVET), or arterial dilation. Ideally, an indexing measurement would be performed at most once every 8-hours, as this time period corresponds with a typical nursing shift. In this case, the nurse would index a patient at the beginning of the shift using the oscillometric approach described herein. As shown in FIG. 24, the indexing measurement typically takes less than 1 minute, and is performed with a cuff-based system that seamlessly integrates with the body-worn monitor used to make the cNIBP measurements. After the indexing measurement, the cuff-based system is removed, and all follow-on cNIBP measurements are made cufflessly using only the ECG and PPG waveforms. At the 8-hour mark, the cuff-based system is reapplied to the patient, and the process is repeated. At this point the subject's arterial properties and value for SYS, DIA, and MAP are recalculated and used for all subsequent measurements that take place over the next 8 hours.

Effect of Motion on PPG and ECG Waveforms

Motion is a parameter that confounds measurement of all vital signs, and is particularly detrimental to optical measurements, such as those used in the Composite Method for cNIBP and pulse oximetry. For this reason it is important for the body-worn monitor to both recognize motion and, ideally, accurately determine the vital sign in its presence.

In a preferred embodiment, motion, posture, arm height, and activity level are determined from a patient by analyzing signals from three separate accelerometers integrated within the body-worn monitor. As shown in detail in FIG. 24, the accelerometers are integrated into the monitor's cabling and wrist-worn transceiver. Each measures three unique signals, each corresponding to the x, y, and z-axes of the body portion to which the accelerometer attaches. These signals are then processed with a series of algorithms, some of which are described in the following patent application, the contents of which are incorporated herein by reference: BODY-WORN VITAL SIGN MONITOR WITH SYSTEM FOR DETECTING AND ANALYZING MOTION (U.S. Ser. No. 12/469,094; filed May 20, 2009). A software framework generates a series of alarms/alerts based on threshold values that are either preset or determined in real time. The framework additionally includes a series of 'heuristic' rules that take the patient's activity state and motion into account, and process the vital signs accordingly. These rules, for example, indicate that a walking patient is likely breathing and has a regular heart rate, even if their motion-corrupted vital signs suggest otherwise. They are described in the following patent application, the contents of which are fully incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009).

Measuring cNIBP During Motion

Figure 15:
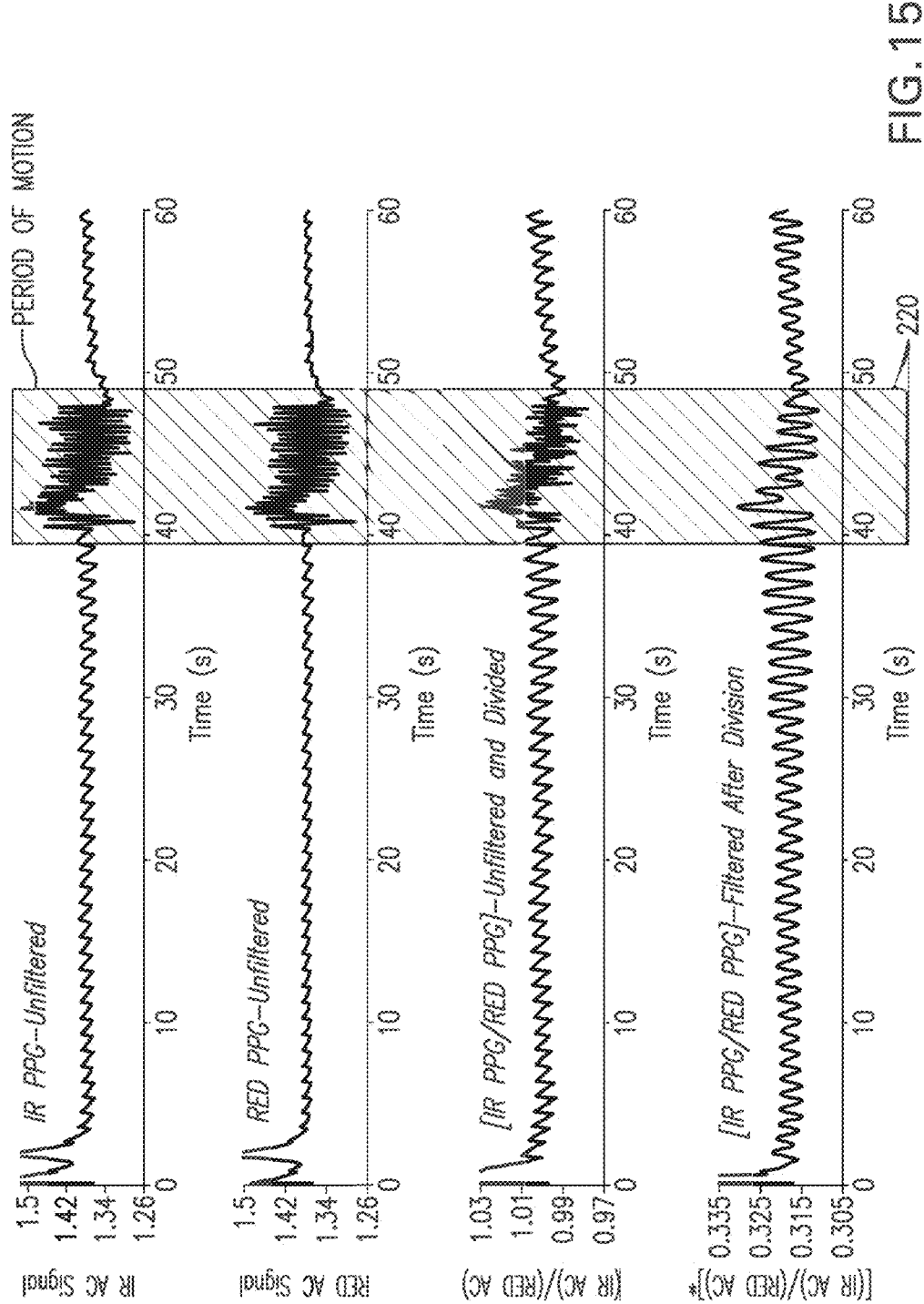
FIG. 15 shows a graph of a time-dependent PPG waveform measured with and without motion using an IR LED (top trace), a RED LED (second trace), the waveform measured with the IR LED divided by the waveform measured with the RED LED (third trace), and the third trace processed with a digital bandpass filter (fourth trace)
Figure 16:
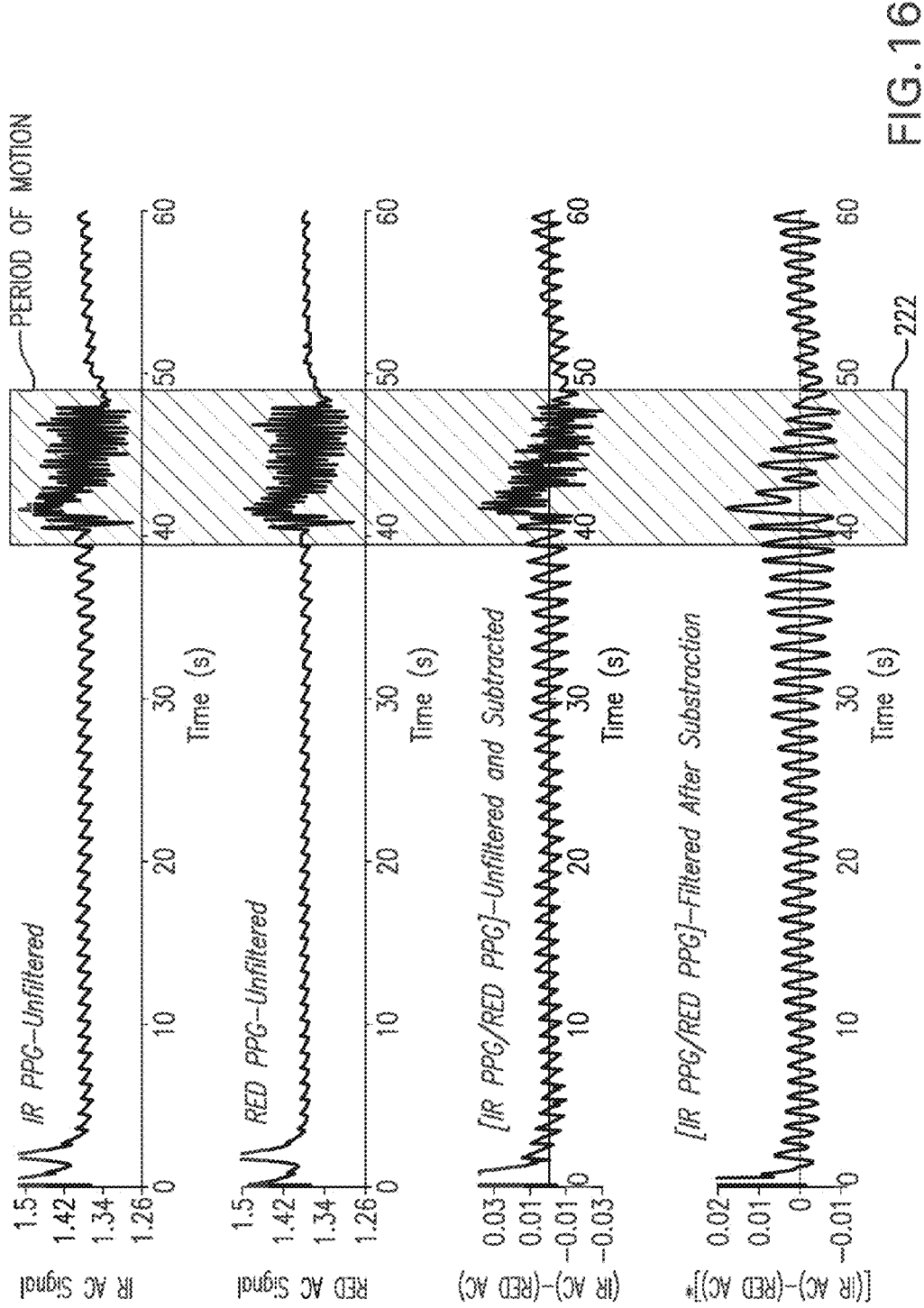
FIG. 16 shows a graph of a time-dependent PPG waveform measured with and without motion using an IR LED (top trace), a RED LED (second trace), the waveform measured with the RED LED subtracted from the waveform measured with the IR LED (third trace), and the third trace processed with a digital bandpass filter (fourth trace)
Figure 17:
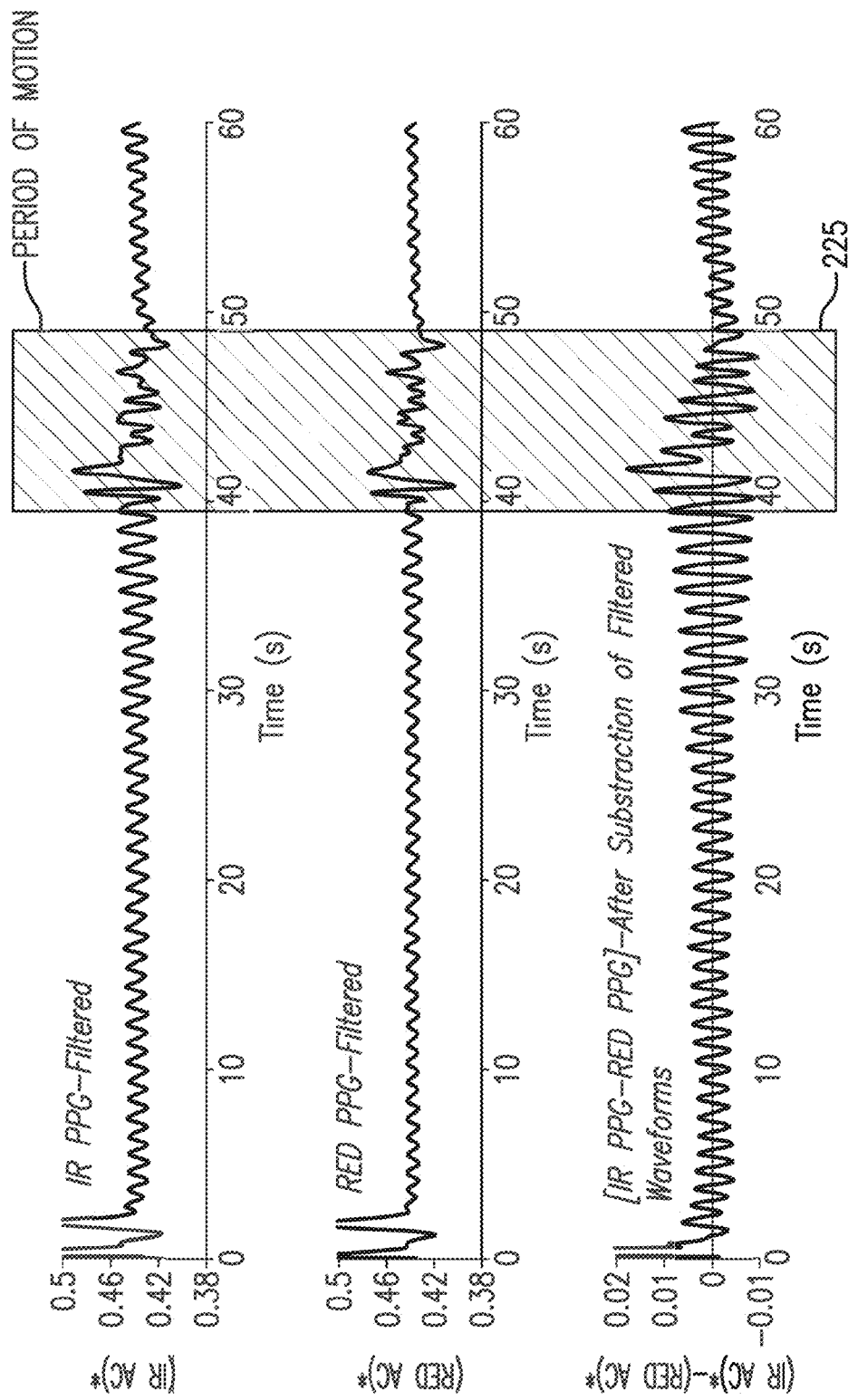
FIG. 17 shows a graph of a time-dependent PPG waveform measured with and without motion using an IR LED and processed with a digital bandpass filter (top trace), a RED LED and processed with a digital bandpass filter (second trace), and the second trace subtracted from the first trace (third trace)

A variety of techniques can be used to remove motion artifacts from signals used to measure cNIBP, and particularly from the PPG waveform used in this measurement. For example, as described in detail below, a single thumb-worn sensor measures PPG waveforms with both red (~660 nm) and infrared (~905 nm) wavelengths to determine an SpO2 measurement. Both PPGs waveforms are affected by motion, and can be collectively processed to remove motion artifacts to some degree. FIGS. 15-17 show results from this analysis. FIG. 15, for example, shows both IR (top trace) and RED (second trace) PPG waveforms measured as a function of time over a 60-second period. Both waveforms were simultaneously measured from the base of the patient's thumb using the sensor shown in FIG. 24. Each waveform features a series of pulses, similar to those shown in FIG. 7A, indicating a heartbeat-induced volumetric expansion in vasculature lying beneath the optical sensor located at the base of the patient's thumb. A period of motion beginning at about 40 seconds and lasting for about 10 seconds, and indicated with the box 220, corrupts both PPG waveforms to the point that a clear, well-defined pulse cannot be measured. In this case, motion consisted of rapid, large-scale motion of the patient's hand. The third trace in FIG. 15 shows the IR PPG waveform divided by the RED PPG waveform. Division reduces the relative amplitudes between motion artifacts shown in the box 220 and the heartbeat-induced pulses shown before and after this period, although not to the point that individual pulses can be determined during the period of motion. However, processing the divided signal with a digital bandpass filter yields a resultant signal shown in the bottom trace that has clear, well-defined pulses. In this case, the bandpass filter was implemented with an IIR response function with a bandpass ranging from 0.001→5 Hz. The resultant pulses, while still somewhat distorted by motion, may be used to determine a PTT and consequently a cNIBP measurement.

FIG. 16 shows a similar result. In this case, however, the RED PPG is subtracted from the IR PPG to yield the third trace. Here, the relative amplitude between heartbeat-induced pulses (shown before and after the box 222 indicating the period of motion) and the motion-affected signal is slightly larger than that resulting from division, as shown in FIG. 15, indicating that subtraction may be preferable to division for this algorithm. The resultant signal is processed with the same digital bandpass filter described above to yield the bottom trace in the figure. Again, such processing yields pulses with reasonable signal-to-noise ratios, even in the presence of substantial motion. Following this processing, pulses within the resultant PPG may be used to determine cNIBP, as described above.

Importantly, collective processing of both the RED and IR PPGs signals, combined with digital filtering, is significantly more effective at removing motion artifacts than simply filtering the signals by themselves. FIG. 17, for example, shows both the IR (top trace) and RED (second trace) PPG waveforms following processing with the same digital bandpass filter used to generate the data shown in FIGS. 15 and 16. In this case the period of motion is indicated by the box 225. Even after processing, these waveforms lack any clear, well-defined pulses during the period of motion. This indicates that filtering a single waveform is likely not adequate for removing motion-induced artifacts. Such waveforms, for example, would not be suitable for PTT-based cNIBP measurements. In contrast, the third trace in FIG. 17 shows the filtered PPG waveforms after the RED PPG is subtracted from the IR PPG. In this case no additional filtering is performed. The resultant waveform, like those shown in the bottom traces of FIGS. 15 and 16, features well-defined pulses that can be subsequently processed to determine PTT-based cNIBP.

Figure 18:
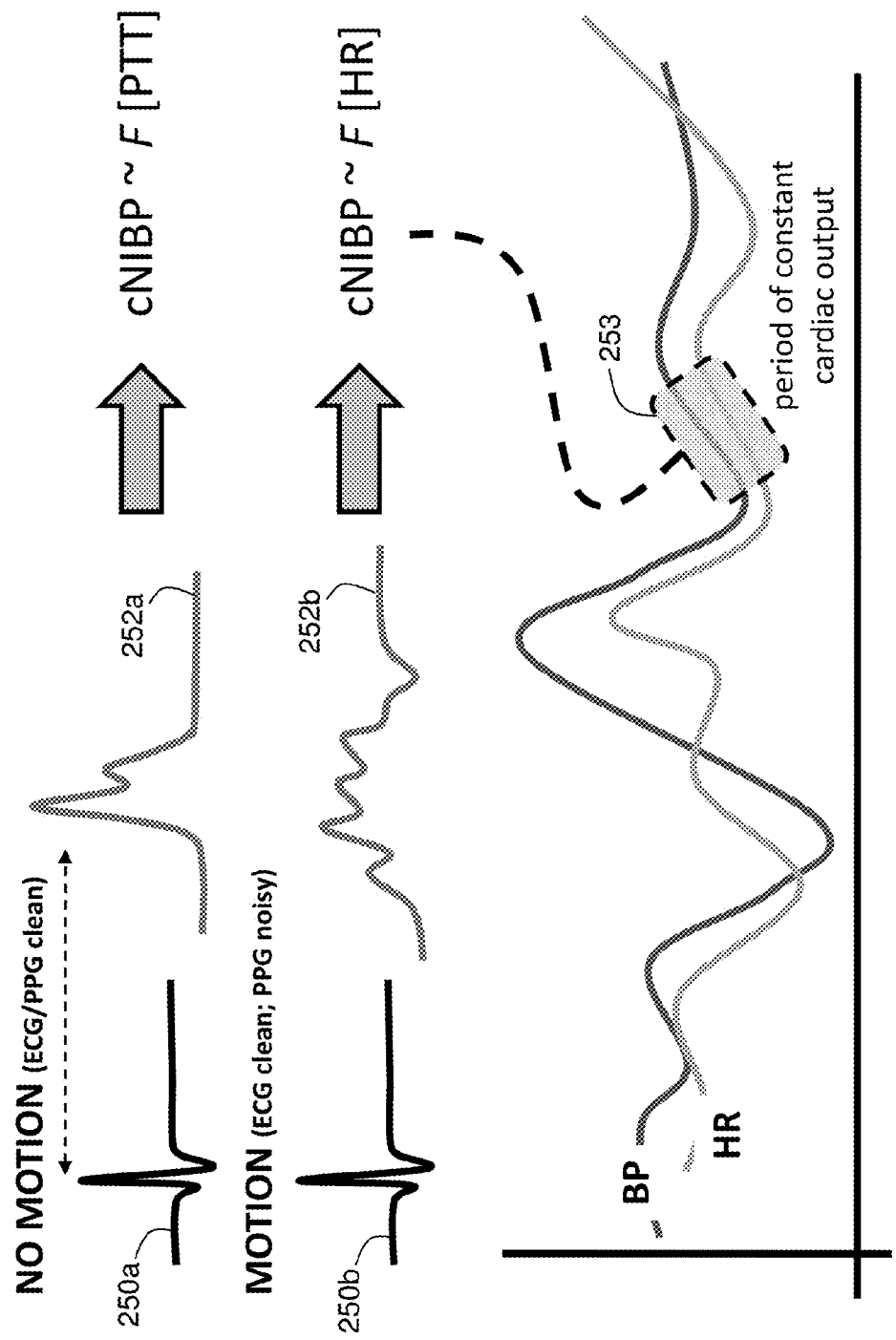
FIG. 18 shows a schematic drawing indicating an algorithm that allows cNIBP measurements to be made in both the presence and absence of motion.
Figure 19:
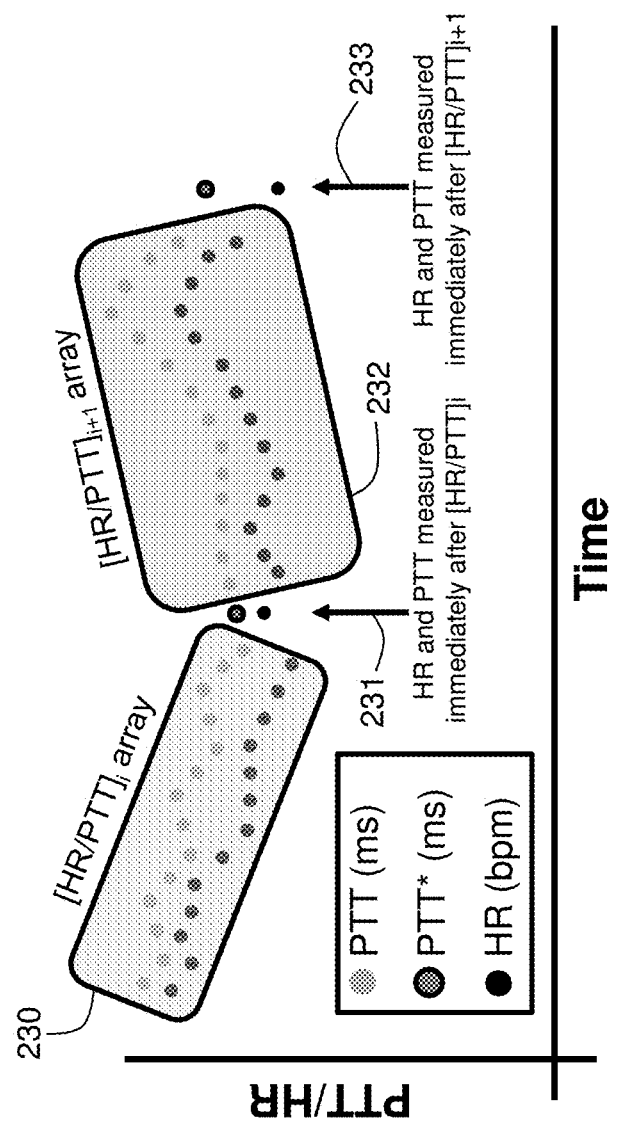
FIG. 19 shows a graph of time-dependent PTT and HR measurements, and how these can be processed with the algorithm shown in FIG. 18 to measure cNIBP in presence of motion.

FIGS. 18 and 19 show an alternative method for collectively using both ECG 250a,b and PPG 252a,b waveforms to measure cNIBP in the presence of motion. This method is based on the fundamental principal that ECG waveforms 250a,b, which rely on electrical signals measured from the patient's chest, are relatively immune from motion artifacts, making it relatively easy to measure HR values therefrom even when large-scale motion is present. In contrast, PPG waveforms 252a,b measured with optical means are relatively susceptible to motion artifacts. Similar to the method described above, it is the collective processing of these signals that yields accurate cNIBP measurement even when the patient is moving.

Collective processing of both HR and PTT determined from ECG and PPG waveforms yields a methodology for approximating PTT during periods of motion. This algorithm features analyzing the patient's current HR and a preceding array of paired values of HR/PTT using a continuous linear fitting approach, and then using these parameters resulting from the fit to estimate PTT. The theory behind the algorithm is as follows. Referring to FIG. 18, when no motion is present both the ECG 250a and PPG 252a waveforms are relatively noise-free. In this case cNIBP is determined from PTT (i.e. cNIBP~F[PTT]) using the Composite Method, which processes the time separating the QRS complex within the ECG 250a and the base of the PPG waveform 252a. When motion is present, the ECG waveform 250b remains relatively noise-free, but the PPG waveform 252b is corrupted by noise. In this case, cNIBP is calculated from HR (i.e. cNIBP~F[HR]) using a real-time, evolving relationship between these two parameters. As indicated by the graph in the lower portion of FIG. 18, HR and PTT have little correlation when evaluated over long periods of time (e.g. 10 minutes or longer), but can have reasonable (or in fact very good) correlations when evaluated over very short periods of time (e.g. less than 2 minutes). Such correlation is indicated by the box 253. This is because cardiac output, which relates HR and cNIBP, is typically constant for these short periods. FIG. 19 illustrates this principal in more detail. As shown by the boxes 230, 232, a relationship between HR and PTT can be determined by analyzing a preceding array of paired HR/PTT values, collected when the patient is not moving, with a simple linear regression model. These arrays, shown in the figure as [HR/PTT]$_i$ and [HR/PTT]$_{i+1}$, are collected over a period ΔT, which is typically between 20 and 60 seconds. The linear model used to fit the array returns a corresponding slope ($M_{HR/PTT,i}$), y-intercept ($B_{HR/PTT,i}$), and correlation value ($r^2_{HR/PTT,i}$). At a subsequent time, indicated by the arrows 231, 233, the patient begins to move and parameters from the linear model can be used along with a current, motion-immune HR value to estimate a value of PTT called an 'effective' PTT (PTT*). Specifically, PTT* is calculated using Equation (12) below, and then used in place of PTT to calculate cNIBP as described above.

$$PTT^* = HR \times M_{HR/PTT,i} + B_{HR+PTT,i} \quad (12)$$

The relationship between HR and PTT determined with the linear model is most accurate when the HR and PTT data points are collected immediately prior to the period of motion. If patient motion continues, then this model can be used along with HR for a period of time of up to 5 minutes to calculate cNIBP values. If patient motion persists past this period, then cNIBP cannot typically be accurately calculated, and this methodology should not be used. Typically this approach works best if correlation between HR and PTT, as indicated by $r^2_{HR/PTT,i}$, is relatively strong. In preferred embodiments, $r^2_{HR/PTT,i}$ is greater than about 0.5 for the algorithm to be implemented. If $r^2_{HR/PTT,i}$ is less than this value the algorithm is not implemented, and a blood pressure value is assumed to be corrupted by motion, and thus not reported.

FIGS. 20A,B and 21A,B indicate the efficacy of this approach. FIGS. 20A and 21A show time-dependent traces of SYS, measured with a femoral A-line, and a 'reconstructed' SYS determined using Equation (11). These graphs were generated using data measured during the 23-subject ICU study, described above. FIGS. 20B and 21B plot the same data in FIGS. 20A and 21A in a different way, showing a point-to-point correlation between SYS measured with the femoral arterial line and 'reconstructed' SYS measured with the method according to the invention. As is clear from these graphs, reconstructing SYS values using this approach yields better agreement and higher correlation when the subject's blood pressure undergoes only small amounts of volatility. For example, FIGS. 20A,B show the 'best' results from the group of 23 subjects. Here, the subject's blood pressure is relatively stable, and the reconstructed SYS agrees extremely well with SYS measured using the femoral arterial line (STDEV=2.0 mmHg; BIAS=0.2 mmHg). FIGS. 21A,B show data from a subject with highly volatile blood pressure. This case represents the 'worst' agreement for the 23 subjects, likely because the volatility in cNIBP also results in a corresponding volatility in cardiac output. This, in turn, makes it more difficult to accurately reconstruct the subject's cNIBP, and results in slightly worse correlation (STDEV=15.8 mmHg; BIAS=0.6 mmHg) between arterial line and reconstructed SYS.

Processing Accelerometer Waveforms to Determine Posture

Figure 22:
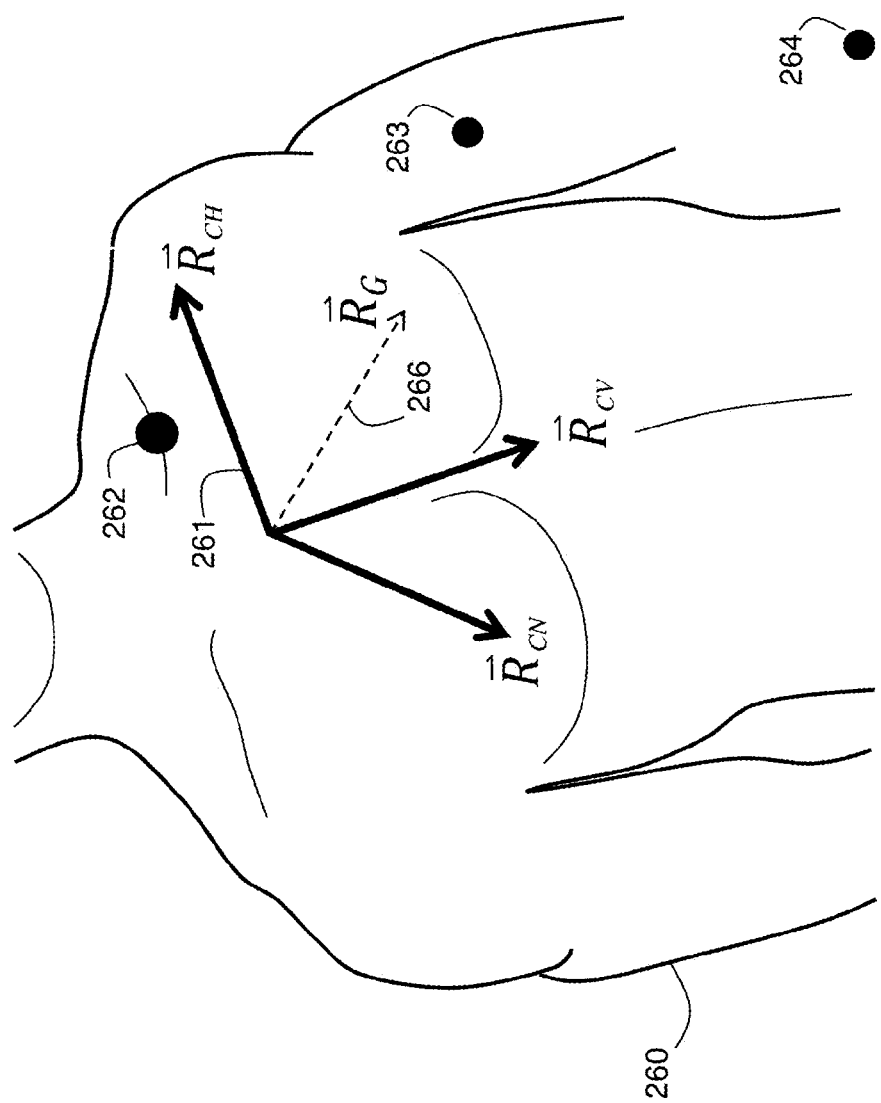
FIG. 22 shows a schematic view of a patient and a coordinate axis used with an algorithm and accelerometer waveforms to determine the patient's posture.

In addition to motion, a patient's posture can influence how the above-described system generates alarms/alerts from cNIBP and other vital signs. For example, the alarms/alerts related to cNIBP may vary depending on whether the patient is lying down or standing up. FIG. 22 indicates how the body-worn monitor can determine motion-related parameters (e.g. degree of motion, posture, and activity level) from a patient 110 using time-dependent accelerometer waveforms continuously generated from the three accelerometers 262, 263, 264 worn, respectively, on the patient's chest, bicep, and wrist. The height of the patient's arm can affect the cNIBP measurement, as blood pressure can vary significantly due to hydrostatic forces induced by changes in arm height. Moreover, this phenomenon can be detected and exploited to calibrate the cNIBP measurement, as described in detail in the above-referenced patent application, the contents of which have been previously incorporated by reference: BODY-WORN VITAL SIGN MONITOR WITH SYSTEM FOR DETECTING AND ANALYZING MOTION (U.S. Ser. No. 12/469,094; filed May 20, 2009). As described in this document, arm height can be determined using DC signals from the accelerometers 263, 264 disposed, respectively, on the patient's bicep and wrist. Posture, in contrast, can be exclusively determined by the accelerometer 262 worn on the patient's chest. An algorithm operating on the wrist-worn transceiver extracts DC values from waveforms measured from this accelerometer and processes them with an algorithm described below to determine posture.

Specifically, torso posture is determined for a patient 260 using angles determined between the measured gravitational vector and the axes of a torso coordinate space 261. The axes of this space 261 are defined in a three-dimensional Euclidean space where $\vec{R}_{CV}$ is the vertical axis, $\vec{R}_{CH}$ is the horizontal axis, and $\vec{R}_{CN}$ is the normal axis. These axes must be identified relative to a 'chest accelerometer coordinate space' before the patient's posture can be determined.

The first step in determining a patient's posture is to identify alignment of $\vec{R}_{CV}$ in the chest accelerometer coordinate space. This can be determined in either of two approaches.

In the first approach, $\vec{R}_{CV}$ is assumed based on a typical alignment of the body-worn monitor relative to the patient. During a manufacturing process, these parameters are then preprogrammed into firmware operating on the wrist-worn transceiver. In this procedure it is assumed that accelerometers within the body-worn monitor are applied to each patient with essentially the same configuration. In the second approach, $\vec{R}_{CV}$ is identified on a patient-specific basis. Here, an algorithm operating on the wrist-worn transceiver prompts the patient (using, e.g., video instruction operating on the wrist-worn transceiver, or audio instructions transmitted through a speaker) to assume a known position with respect to gravity (e.g., standing upright with arms pointed straight down). The algorithm then calculates $\vec{R}_{CV}$ from DC values corresponding to the x, y, and z axes of the chest accelerometer while the patient is in this position. This case, however, still requires knowledge of which arm (left or right) the monitor is worn on, as the chest accelerometer coordinate space can be rotated by 180 degrees depending on this orientation. A medical professional applying the monitor can enter this information using the GUI, described above. This potential for dual-arm attachment requires a set of two pre-determined vertical and normal vectors which are interchangeable depending on the monitor's location. Instead of manually entering this information, the arm on which the monitor is worn can be easily determined following attachment using measured values from the chest accelerometer values, with the assumption that $\vec{R}_{CV}$ is not orthogonal to the gravity vector.

The second step in the procedure is to identify the alignment of $\vec{R}_{CN}$ in the chest accelerometer coordinate space. The monitor determines this vector in the same way it determines $\vec{R}_{CV}$ using one of two approaches. In the first approach the monitor assumes a typical alignment of the chest-worn accelerometer on the patient. In the second approach, the alignment is identified by prompting the patient to assume a known position with respect to gravity. The monitor then calculates $\vec{R}_{CN}$ from the DC values of the time-dependent accelerometer waveform.

The third step in the procedure is to identify the alignment of $\vec{R}_{CH}$ in the chest accelerometer coordinate space. This vector is typically determined from the vector cross product of $\vec{R}_{CV}$ and $\vec{R}_{CN}$, or it can be assumed based on the typical alignment of the accelerometer on the patient, as described above.

A patient's posture is determined using the coordinate system described above and in FIG. 22, along with a gravitational vector $\vec{R}_G$ that extends normal from the patient's chest. The angle between $\vec{R}_{CV}$ and $\vec{R}_G$ is given by equation (13):

$$\theta_{VG}[n] = \arccos\left(\frac{\vec{R}_G[n] \cdot \vec{R}_{CV}}{\|\vec{R}_G[n]\|\|\vec{R}_{CV}\|}\right) \quad (13)$$

where the dot product of the two vectors is defined as:

$$\vec{R}_G[n] \cdot \vec{R}_{CV} = (y_{Cx}[n] \times r_{CVx}) + (y_{Cy}[n] \times r_{CVy}) + (y_{Cz}[n] \times r_{CVz}) \quad (14)$$

The definition of the norms of $\vec{R}_G$ and $\vec{R}_{CV}$ are given by equations (15) and (16):

$$\|\vec{R}_G[n]\| = \sqrt{(y_{Cx}[n])^2 + (y_{Cy}[n])^2 + (y_{Cz}[n])^2} \quad (15)$$

$$\|\vec{R}_{CV}\| = \sqrt{(r_{CVx})^2 + (r_{CVy})^2 + (r_{CVz})^2} \quad (16)$$

As indicated in equation (5), the monitor compares the vertical angle $\theta_{VG}$ to a threshold angle to determine whether the patient is vertical (i.e. standing upright) or lying down:

if $\theta_{VG} \leq 45°$ then Torso State=0, the patient is upright (17)

If the condition in equation (17) is met the patient is assumed to be upright, and their torso state, which is a numerical value equated to the patient's posture, is equal to 0. The patient is assumed to be lying down if the condition in equation (17) is not met, i.e. $\theta_{VG} > 45$ degrees. Their lying position is then determined from angles separating the two remaining vectors, as defined below.

The angle $\theta_{NG}$ between $\vec{R}_{CN}$ and $\vec{R}_G$ determines if the patient is lying in the supine position (chest up), prone position (chest down), or on their side. Based on either an assumed orientation or a patient-specific calibration procedure, as described above, the alignment of $\vec{R}_{CN}$ is given by equation (18), where i, j, k represent the unit vectors of the x, y, and z axes of the chest accelerometer coordinate space respectively:

$$\vec{R}_{CN} = r_{CNx}\hat{i} + r_{CNy}\hat{j} + r_{CNz}\hat{k} \quad (18)$$

The angle between $\vec{R}_{CN}$ and $\vec{R}_G$ determined from DC values extracted from the chest accelerometer waveform is given by equation (19):

$$\theta_{NG}[n] = \arccos\left(\frac{\vec{R}_G[n] \cdot \vec{R}_{CN}}{\|\vec{R}_G[n]\|\|\vec{R}_{CN}\|}\right) \quad (19)$$

The body-worn monitor determines the normal angle $\theta_{NG}$ and then compares it to a set of predetermined threshold angles to determine which position the patient is lying in, as shown in equation (20):

if $\theta_{NG} \leq 35°$ then Torso State=1, the patient is supine if $\theta_{NG} \geq 135°$ then Torso State=2, the patient is prone (20)

If the conditions in equation (20) are not met then the patient is assumed to be lying on their side. Whether they are lying on their right or left side is determined from the angle calculated between the horizontal torso vector and measured gravitational vectors, as described above.

The alignment of $\vec{R}_{CH}$ is determined using either an assumed orientation, or from the vector cross-product of $\vec{R}_{CV}$ and $\vec{R}_{CN}$ as given by equation (21), where i, j, k represent the unit vectors of the x, y, and z axes of the accelerometer coordinate space respectively. Note that the orientation of the calculated vector is dependent on the order of the vectors in the operation. The order below defines the horizontal axis as positive towards the right side of the patient's body.

$$\vec{R}_{CH} = r_{CVx}\hat{i} + r_{CVy}\hat{j} + r_{CVz}\hat{k} = \vec{R}_{CV} \times \vec{R}_{CN} \quad (21)$$

The angle $\theta_{HG}$ between $\vec{R}_{CH}$ and $\vec{R}_G$ is determined using equation (22):

$$\theta_{HG}[n] = \arccos\left(\frac{\vec{R}_G[n] \cdot \vec{R}_{CH}}{\|\vec{R}_G[n]\| \|\vec{R}_{CH}\|}\right) \quad (22)$$

The monitor compares this angle to a set of predetermined threshold angles to determine if the patient is lying on their right or left side, as given by equation (23):

if $\theta_{HG} \geq 90°$ then Torso State=3, the patient is on their right side if $\theta_{NG} < 90°$ then Torso State=4, the patient is on their left side (23)

Table 1 describes each of the above-described postures, along with a corresponding numerical torso state used to render, e.g., a particular icon on a remote computer:

TABLE 1 postures and their corresponding torso states

| Posture | Torso State |
|---|---|
| standing upright | 0 |
| supine: lying on back | 1 |
| prone: lying on chest | 2 |
| lying on right side | 3 |
| lying on left side | 4 |
| undetermined posture | 5 |

Figure 23A:
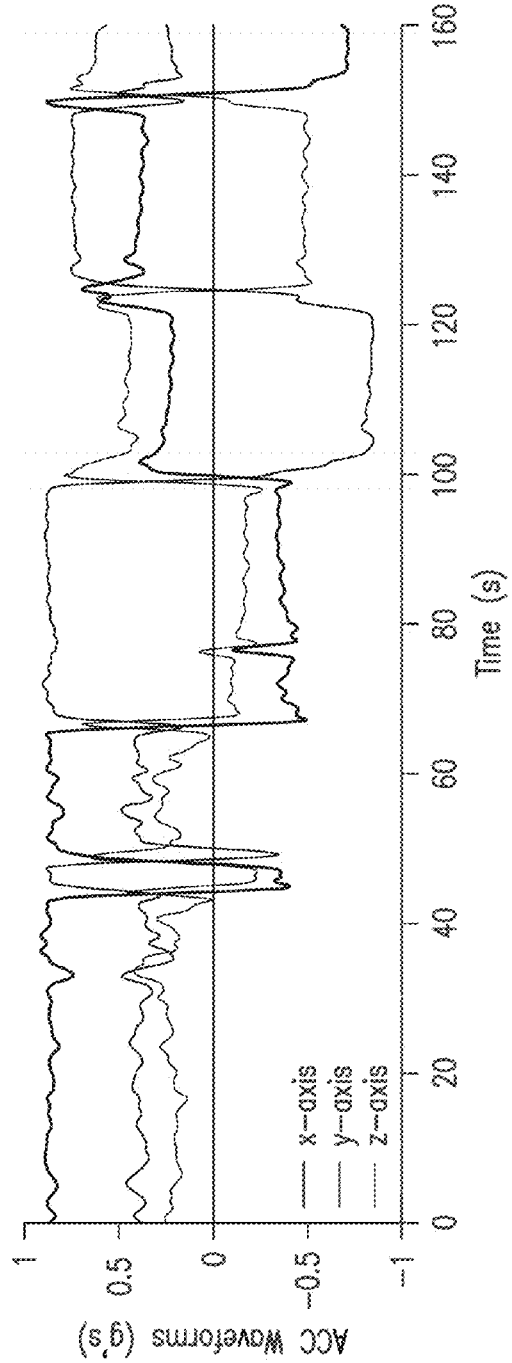
FIG. 23A shows a graph of time-dependent accelerometer waveforms measured from a patient's chest during different postures.
Figure 23B:
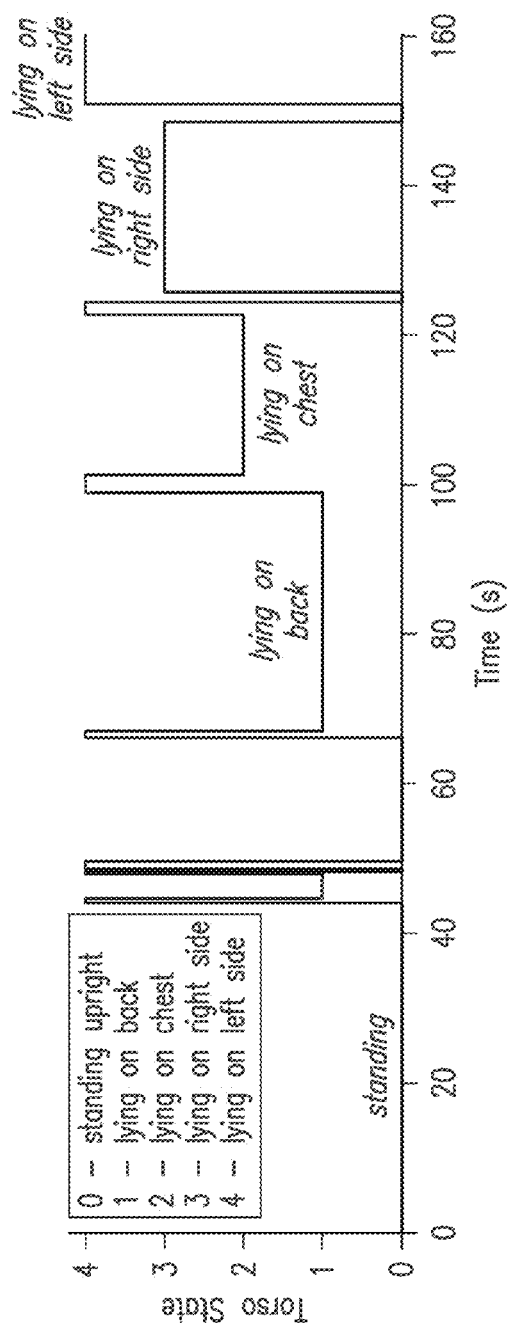
FIG. 23B shows a graph of time-dependent postures determined by processing the accelerometer waveforms of FIG. 23A with an algorithm and the coordinate axis shown in FIG. 22.

FIGS. 23A and 23B show, respectively, graphs of time-dependent accelerometer waveforms measured along the x, y, and z-axes (FIG. 23A), and the torso states (i.e. postures; FIG. 23B) determined from these waveforms for a moving patient, as described above. As the patient moves, the DC values of the accelerometer waveforms measured by the chest accelerometer vary accordingly, as shown in FIG. 23A. The body-worn monitor processes these values as described above to continually determine $\vec{R}_G$ and the various quantized torso states for the patient, as shown in FIG. 23B. The torso states yield the patient's posture as defined in Table 1. For this study the patient rapidly alternated between standing, lying on their back, chest, right side, and left side within a time period of about 160 seconds. As described above, different alarm/alert conditions (e.g. threshold values) for vital signs can be assigned to each of these postures, or the specific posture itself may result in an alarm/alert. Additionally, the time-dependent properties of the graph can be analyzed (e.g. changes in the torso states can be counted) to determine, for example, how often the patient moves in their hospital bed. This number can then be equated to various metrics, such as a 'bed sore index' indicating a patient that is so stationary in their bed that lesions may result. Such a state could then be used to trigger an alarm/alert to the supervising medical professional.

Body-Worn Monitor for Measuring cNIBP

Figures 24A, 24B:
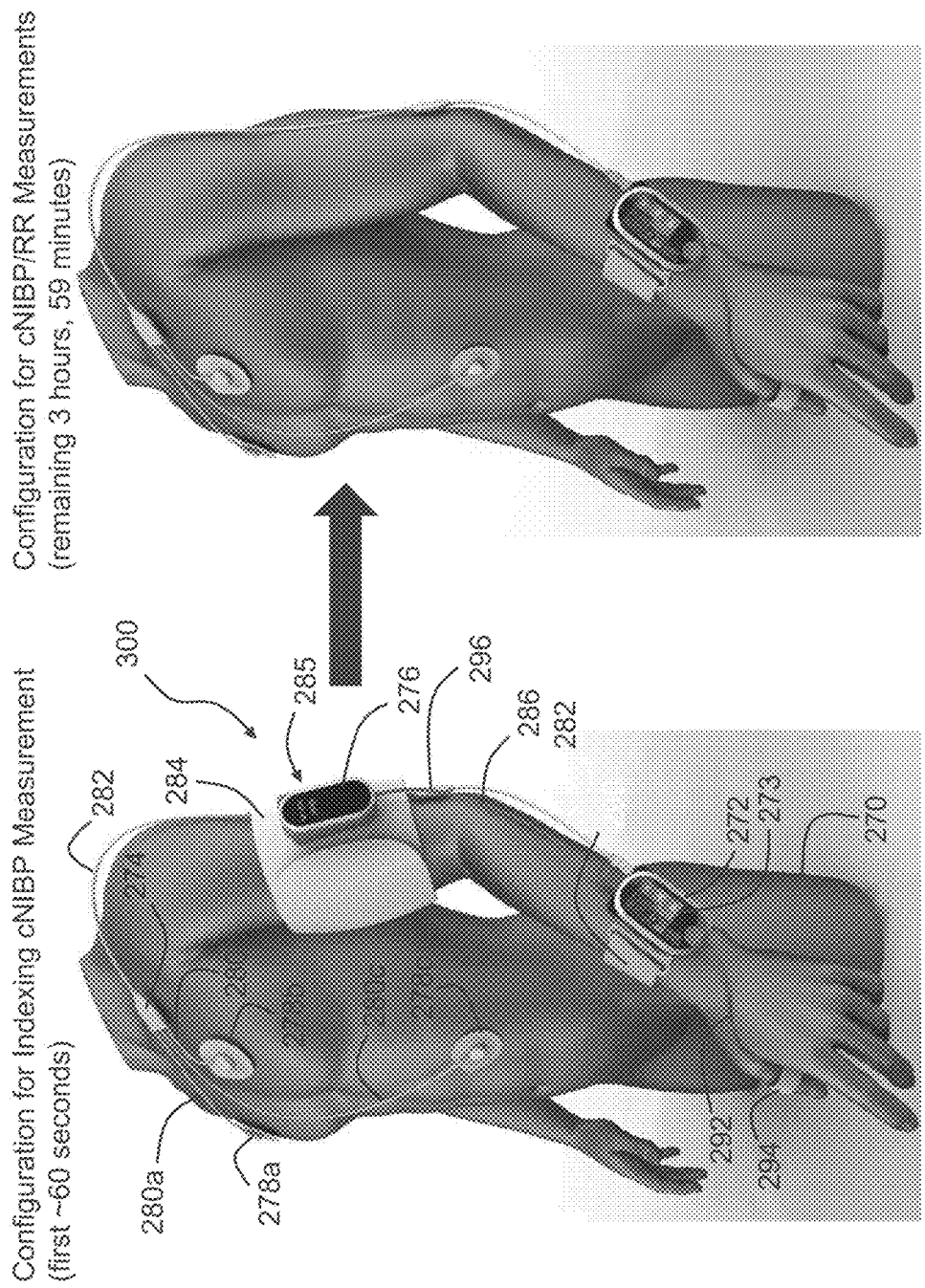
FIG. 24A shows a three-dimensional image of the body-worn monitor of the invention attached to a patient during the indexing portion of the Composite Method, and includes a pneumatic system.
FIG. 24B shows a three-dimensional image of the body-worn monitor of the invention attached to a patient after an initial indexing measurement.

FIGS. 24A and 24B show how the body-worn monitor 300 described above attaches to a patient 270 to measure cNIBP and other vital signs. A detailed description of this monitor is provided by the following co-pending patent application, the contents of which are incorporated herein by reference: BODY-WORN VITAL SIGN MONITOR (U.S. Ser. No. 12/560,087; filed Sep. 15, 2009). These figures show two configurations of the system: FIG. 24A shows the system used during the indexing portion of the Composite Method, and includes a pneumatic, cuff-based system 285, while FIG. 24B shows the system used for subsequent cNIBP measurements. The indexing measurement typically takes about 60 seconds, and is typically performed once every 4 hours. Once the indexing measurement is complete the cuff-based system 285 is typically removed from the patient. The remainder of the time the monitor 300 performs the cNIBP measurements.

Figure 25:
FIG. 25 shows a three-dimensional image of the wrist-worn transceiver used with the body-worn monitor of FIGS. 24A and 24B.

The body-worn monitor 300 features a wrist-worn transceiver 272, described in more detail in FIG. 25, featuring a touch panel interface 273 that displays cNIBP values and other vital signs. A wrist strap 290 affixes the transceiver 272 to the patient's wrist like a conventional wristwatch. A flexible cable 292 connects the transceiver 272 to a pulse oximeter probe 294 that wraps around the base of the patient's thumb. During a measurement, the probe 294 generates a time-dependent PPG waveform which is processed along with an ECG to measure cNIBP and SpO2. This provides an accurate representation of blood pressure in the central regions of the patient's body, as described above.

To determine accelerometer waveforms the body-worn monitor 300 features three separate accelerometers located at different portions on the patient's arm and chest. The first accelerometer is surface-mounted on a circuit board in the wrist-worn transceiver 272 and measures signals associated with movement of the patient's wrist. As described above, this motion can also be indicative of that originating from the patient's fingers, which will affect the SpO2 measurement. The second accelerometer is included in a small bulkhead portion 296 included along the span of the cable 282. During a measurement, a small piece of disposable tape, similar in size to a conventional bandaid, affixes the bulkhead portion 296 to the patient's arm. In this way the bulkhead portion 296 serves two purposes: 1) it measures a time-dependent accelerometer waveform from the mid-portion of the patient's arm, thereby allowing their posture and arm height to be determined as described in detail above; and 2) it secures the cable 282 to the patient's arm to increase comfort and performance of the body-worn monitor 300, particularly when the patient is ambulatory. The third accelerometer is mounted in a bulkhead component 274 that connects through cables 280a-c to ECG electrodes 278a-c. These signals are then digitized, transmitted through the cable 282 to the wrist-worn transceiver 272, where they are processed with an algorithm as described above to determine respiration rate, as described in the following co-pending patent applications, the contents of which are incorporated herein by reference: BODY-WORN MONITOR FOR MEASURING RESPIRATION RATE (U.S. Ser. No. 12/559,442; filed Sep. 14, 2009).

The cuff-based module 285 features a pneumatic system 276 that includes a pump, valve, pressure fittings, pressure sensor, analog-to-digital converter, microcontroller, and rechargeable Li:ion battery. During an indexing measurement, the pneumatic system 276 inflates a disposable cuff 284 and performs two measurements according to the Composite Method: 1) it performs an inflation-based measurement of oscillometry to determine values for $SYS_{INDEX}$, $DIA_{INDEX}$, and $MAP_{INDEX}$; and 2) it determines a patient-specific slope describing the relationship between PTT and MAP. These measurements are described in detail in the above-referenced patent application entitled: 'VITAL SIGN MONITOR FOR MEASURING BLOOD PRESSURE USING OPTICAL, ELECTRICAL, AND PRESSURE WAVEFORMS' (U.S. Ser. No. 12/138,194; filed Jun. 12, 2008), the contents of which have been previously incorporated herein by reference.

The cuff 284 within the cuff-based pneumatic system 285 is typically disposable and features an internal, airtight bladder that wraps around the patient's bicep to deliver a uniform pressure field. During the indexing measurement, pressure values are digitized by the internal analog-to-digital converter, and sent through a cable 286 according to a CAN protocol, along with $SYS_{INDEX}$, $DIA_{INDEX}$, and $MAP_{INDEX}$, to the wrist-worn transceiver 272 for processing as described above. Once the cuff-based measurement is complete, the cuff-based module 285 is removed from the patient's arm and the cable 286 is disconnected from the wrist-worn transceiver 272. cNIBP is then determined using PTT, as described in detail above.

To determine an ECG, the body-worn monitor 300 features a small-scale, three-lead ECG circuit integrated directly into the bulkhead 274 that terminates an ECG cable 282. The ECG circuit features an integrated circuit that collects electrical signals from three chest-worn ECG electrodes 278*a-c* connected through cables 280*a-c*. As described above, the ECG electrodes 278*a-c* are typically disposed in a conventional Einthoven's Triangle configuration which is a triangle-like orientation of the electrodes 278*a-c* on the patient's chest that features three unique ECG vectors. From these electrical signals the ECG circuit determines up to three ECG waveforms, which are digitized using an analog-to-digital converter mounted proximal to the ECG circuit, and sent through the cable 282 to the wrist-worn transceiver 272 according to the CAN protocol. There, the ECG and PPG waveforms are processed to determine the patient's blood pressure. Heart rate and respiration are determined directly from the ECG waveform using known algorithms, such impedance pneumography, as well as those described above. The cable bulkhead 274 also includes an accelerometer that measures motion associated with the patient's chest as described above.

As described above, there are several advantages of digitizing ECG and accelerometer waveforms prior to transmitting them through the cable 282. First, a single transmission line in the cable 282 can transmit multiple digital waveforms, each generated by different sensors. This includes multiple ECG waveforms (corresponding, e.g., to vectors associated with three, five, and twelve-lead ECG systems) from the ECG circuit mounted in the bulkhead 274, along with waveforms associated with the x, y, and z-axes of accelerometers mounted in the bulkheads 274, 296. More sophisticated ECG circuits (e.g. five and twelve-lead systems) can plug into the wrist-worn transceiver to replace the three-lead system shown in FIGS. 24A and 24B.

FIG. 25 shows a close-up view of the wrist-worn transceiver 272. As described above, it attaches to the patient's wrist using a flexible strap 290 which threads through two D-ring openings in a plastic housing 306. The transceiver 272 features a touch panel display 320 that renders a GUI 273 which is altered depending on the viewer (typically the patient or a medical professional). Specifically, the transceiver 272 includes a small-scale infrared barcode scanner 302 that, during use, can scan a barcode worn on a badge of a medical professional. The barcode indicates to the transceiver's software that, for example, a nurse or doctor is viewing the user interface. In response, the GUI 273 displays vital sign data and other medical diagnostic information appropriate for medical professionals. Using this GUI 273, the nurse or doctor, for example, can view the vital sign information, set alarm parameters, and enter information about the patient (e.g. their demographic information, medication, or medical condition). The nurse can press a button on the GUI 273 indicating that these operations are complete. At this point, the display 320 renders an interface that is more appropriate to the patient, such as time of day and battery power.

The transceiver 272 features three CAN connectors 304*a-c* on the side of its upper portion, each which supports the CAN protocol and wiring schematics, and relays digitized data to the internal CPU. Digital signals that pass through the CAN connectors include a header that indicates the specific signal (e.g. ECG, ACC, or pressure waveform from the cuff-based module) and the sensor from which the signal originated. This allows the CPU to easily interpret signals that arrive through the CAN connectors 304*a-c*, such as those described above corresponding to ECG waveforms, and means that these connectors are not associated with a specific cable. Any cable connecting to the transceiver can be plugged into any connector 304*a-c*. As shown in FIG. 24A, the first connector 304*a* receives the cable 282 that transports a digitized ECG waveform determined from the ECG circuit and electrodes, and digitized accelerometer waveforms measured by accelerometers in the cable bulkhead 274 and the bulkhead portion 296 associated with the ECG cable 282.

The second CAN connector 304*b* shown in FIG. 25 receives the cable 286 that connects to the pneumatic cuff-based system 285 used for the pressure-dependent indexing measurement (shown in FIG. 24A). This connector 304*b* receives a time-dependent pressure waveform delivered by the pneumatic system 285 to the patient's arm, along with values for $SYS_{INDEX}$, $DIA_{INDEX}$, and $MAP_{INDEX}$ values determined during the indexing measurement. The cable 286 unplugs from the connector 304*b* once the indexing measurement is complete, and is plugged back in after approximately four hours for another indexing measurement.

The final CAN connector 304*c* can be used for an ancillary device, e.g. a glucometer, infusion pump, body-worn insulin pump, ventilator, or et-CO2 measurement system. As described above, digital information generated by these systems will include a header that indicates their origin so that the CPU can process them accordingly.

The transceiver includes a speaker 301 that allows a medical professional to communicate with the patient using a voice over Internet protocol (VOIP). For example, using the speaker 301 the medical professional could query the patient from a central nursing station or mobile phone connected to a wireless, Internet-based network within the hospital. Or the medical professional could wear a separate transceiver similar to the shown in FIG. 25, and use this as a communication device. In this application, the transceiver 272 worn by the patient functions much like a conventional cellular telephone or 'walkie talkie': it can be used for voice communications with the medical professional and can additionally relay information describing the patient's vital signs and motion. The speaker can also enunciate pre-programmed messages to the patient, such as those used to calibrate the chest-worn accelerometers for a posture calculation, as described above.

Multi-Pixel Sensors for Measuring PPG Waveforms in the Presence of Motion

As described above and shown in FIG. 24A, the thumb-worn sensor typically used in the body-worn monitor features a photodetector with a single-pixel light-detecting region. Typically this pixel has an area of 2-4 mm^2. During the Composite Method, the photodetector measures a PPG waveform, which is collectively processed with the ECG waveform to determine cNIBP. Alternatively, as shown in FIGS. 26-29, an optical sensor 351 featuring a multi-pixel detector 354 can be used in place of a single-pixel detector to measure a PPG waveform. Such a detector 354 may be particularly effective at detecting signals when a patient is in motion.

Figures 26, 27:
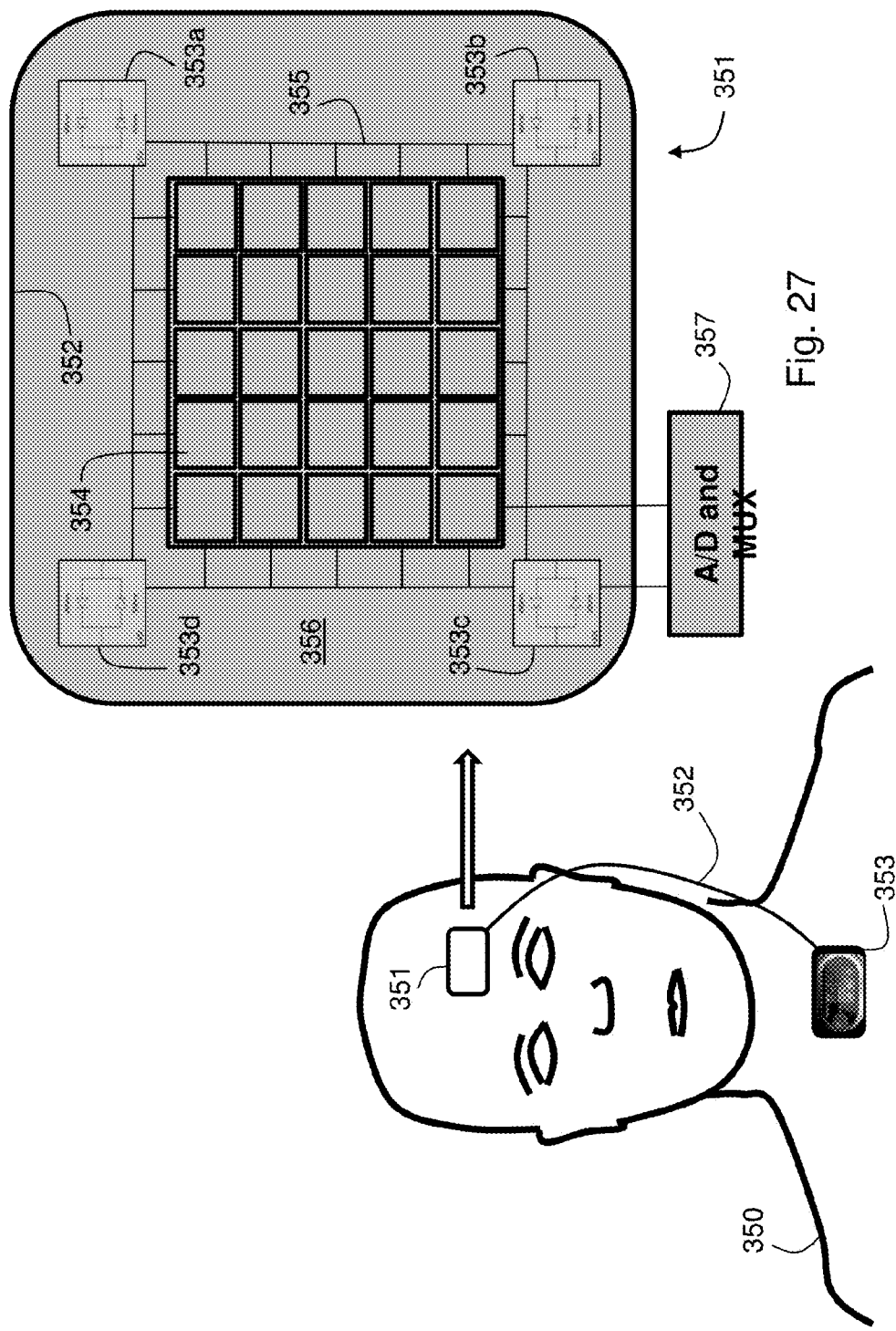
FIG. 26 shows an image of a patient wearing a head-mounted sensor featuring a multi-pixel array photodetector for measuring a PPG waveform according to an alternate embodiment of the invention.
FIG. 27 shows a plan view of the multi-pixel array photodetector of FIG. 26.

The multi-pixel sensor 351 features a soft, flexible substrate 352 coated on its perimeter with an adhesive 356 designed to adhere to a patient's skin. As shown in FIG. 26, for optimal results the sensor 351 is adhered to the forehead of a patient 350, and connects through a cable 352 to a controller 353. In this embodiment, the controller 353 and cable 352 are similar, respectively, to the wrist-worn transceiver 273 and cable 292 shown in FIG. 24A. Experiments indicate that the forehead is the ideal sensor location for this alternative embodiment, presumably because tissue supporting underlying vasculature is relatively thin and buttressed on its inner side with bone from the patient's skull. This physiology minimizes motion between the sensor 351 and arteries in the forehead that can cause artifacts in the PPG. Additionally, presence of the skull limits the compressibility of the thin, underlying tissue, which in turn minimizes motion-induced flow of both blood and interstitial fluids within the tissue. These factors, particularly when coupled with the forehead's large available measurement area relatively small degree of motion, make this location ideal for the sensor 351.

The sensor 351 typically features a square footprint and includes four dual-wavelength LEDs 353a-d positioned in each of its corners. Each LED 353a-d emits both red and infrared optical wavelengths, as described above. An adjustable voltage bias supplied to each LED determines its emitted wavelength. During a measurement, the substrate 352 attaches to the patient's forehead with the adhesive 356, allowing the LEDs 353a-d to deliver a relatively uniform optical field to the tissue underneath. The optical field is partially absorbed by pulsating blood in the underlying vasculature according to the Beer-Lambert law, as described above. This modulates the optical field, which is then detected in a reflection-mode geometry by the multi-pixel detector 354. Each pixel element in the detector 354 typically has an area of 1-2 mm^2, and generates a unique, analog electrical field which propagates through a series of electrical interconnects 355 to an electrical system 357 featuring a multichannel analog-to-digital converter (A/D) coupled to a circuit for multiplexing and demultiplexing (MUX) the resulting digital signals. These components digitize the analog signals from each pixel element and process them to form a single PPG waveform, similar to that shown in FIG. 7A.

Figure 28A:
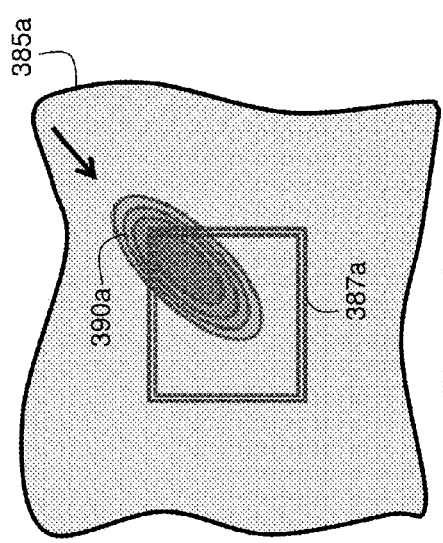
FIG. 28A shows a bolus of blood passing through a detecting area of a conventional single-pixel photodetector for measuring a PPG waveform.
Figure 28B:
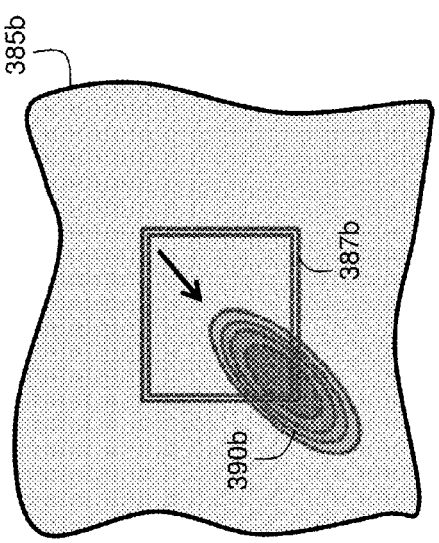
FIG. 28B shows a bolus of blood passing through a detecting area of a conventional single-pixel photodetector for measuring a PPG waveform.

FIGS. 28A,B and 29A,B indicate how the multi-pixel sensor 351a,b (FIGS. 29A,B) may be superior at detecting PPG waveforms during motion when compared to a conventional single-pixel detector 385a,b (FIGS. 28A,B). Blood is a viscoelastic fluid, and during motion will ebb and flow in a patient's arterial system according to Newtonian physics. This affect, informally referred to herein as 'blood sloshing', can be characterized by time-dependent properties (e.g. rise and fall times) that are similar in their frequency makeup to an actual pulse in a PPG waveform. This is why, for example, motion-induced artifacts shown in the waveforms in FIGS. 15 and 16 look similar to the actual pulses in the PPG. Blood sloshing causes a bolus of blood 390a,b to move in and out of the region measured with a single-pixel detector 387a,b shown in FIGS. 28A,B. The single detector 387a,b has no ability to track the time-dependent dynamics of the bolus of blood 390a,b as it moves across the detector field. The bolus 390a moves into the detector field at time to, propagates across the field, and finally moves out at time $t_0+\Delta t$. Because it cannot be isolated, the bolus 390a,b results in an artifact in the PPG waveform that is difficult, if not impossible, to remove with conventional means, such as a digital filter.

Figure 29A:
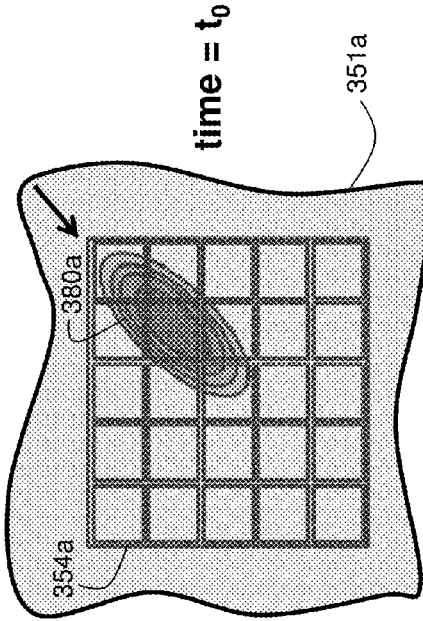
FIG. 29A shows a bolus of blood passing through a detecting area of the multi-pixel array photodetector of FIGS. 26 and 27.
Figure 29B:
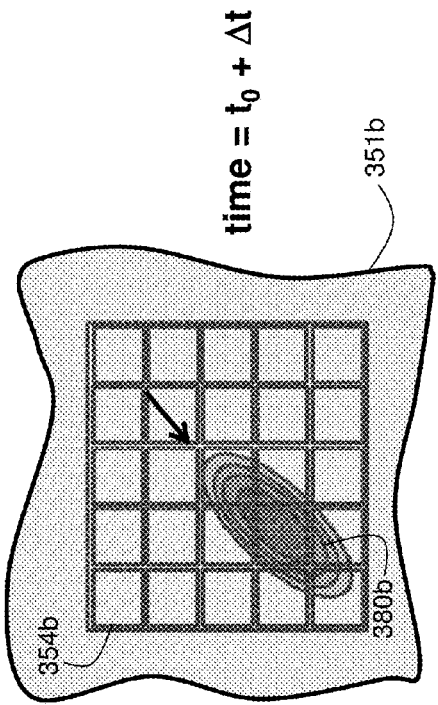
FIG. 29B shows a bolus of blood passing through a detecting area of the multi-pixel array photodetector of FIGS. 26 and 27.

In contrast, FIGS. 29A,B show how a multi-pixel detector 351a,b can track the bolus of blood 380a,b as it moves across the detector area. This allows it to be isolated and removed from the PPG waveform using the multiplexing/demultiplexing circuitry 357 described with reference to FIG. 27. In this case, for example, the bolus 380a,b moves across a diagonal line in the detector field; only pixels lying along this line will yields signals affected by the motion-related artifact. These signals will show different behavior than conventional PPG waveforms, which will be detected by pixels in the upper left-hand and lower right-hand portions of the multi-array detector 354a,b. Once detected, signals from each pixel can be processed with a variety of signal-processing techniques, such as those used to process video images, to deconvolute artifacts arising from the bolus. Ultimately this can yields a relatively noise-free PPG waveform, which can then be processed with the Composite Method to determine cNIBP.

High-Level Algorithm for Measuring All Vital Signs

Figure 30:
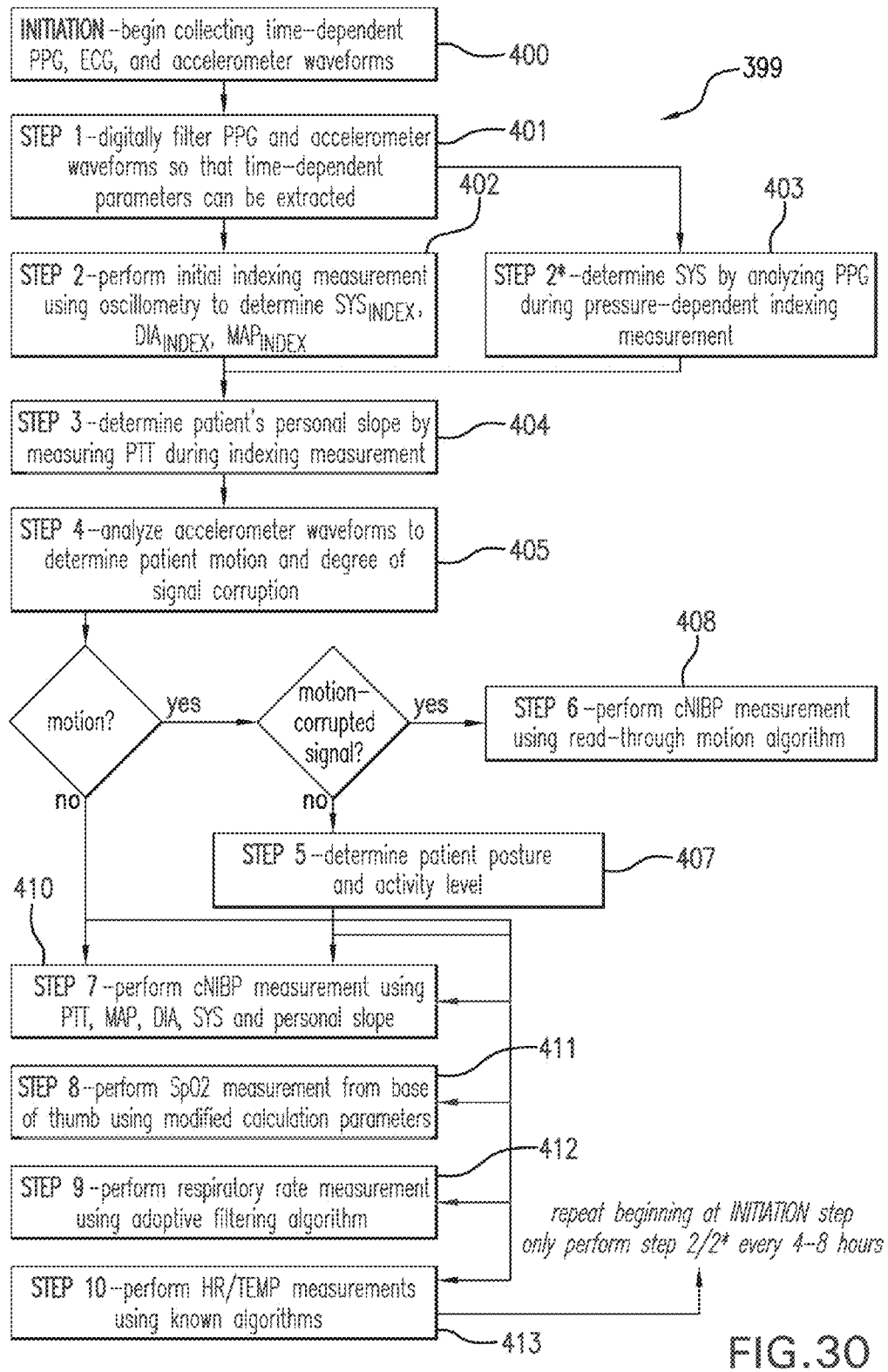
FIG. 30 shows a flow chart for measuring cNIBP, SpO2, respiration rate, heart rate, temperature, and motion according to the invention.

FIG. 30 provides a flow chart that shows a high-level algorithm 399, including the Composite Method, used to monitor vital signs from a hospitalized patient. The initiation phase (step 400) of the algorithm 399 begins with collection of time-dependent PPG, ECG, and accelerometer waveforms using analog and digital circuitry within the body-worn monitor. PPG waveforms are measured using an optical sensor attached to the patient's thumb, while ECG waveforms are measured with a series of electrodes (typically three or five) attached to the patient's chest. Three accelerometers, integrated within the body-worn monitor's cabling and wrist-worn transceiver, each measure three digital accelerometer waveforms corresponding to an x, y, or z-axis. Once collected, the PPG and accelerometer waveforms are digitally filtered (step 401) so that time-dependent properties can be extracted and processed as described in detail above. The pressure waveform, which is generated during an indexing measurement using a pneumatic system and cuff wrapped around the patient's bicep, is measured during inflation and processed using oscillometry to determine $SYS_{INDEX}$, $DIA_{INDEX}$, and $MAP_{INDEX}$ values (step 402). Alternatively, $SYS_{INDEX}$ can be determined directly by processing the PPG in the presence of applied pressure during the indexing measurement, as described above with reference to FIG. 8 (step 403). PTT is measured as a function of applied pressure during the indexing measurement, and is processed to determine a personal, patient-specific slope (step 404). Motion can complicate measurement of the above-described parameters, and is determined by processing time-dependent signals from the three accelerometers attached to the patient and connected to the body-worn monitor. These signals are collected and processed to determine the degree of motion-based signal corruption (step 405), and to additionally determine the patient's posture and activity level (step 407). If motion is determined to be present, cNIBP can be estimated using the read-through motion algorithm described above with reference to FIGS. 18 and 19 (step 408).

When minimal or no motion is present, the patient-specific slope, along with blood pressure values determined with oscillometry during the indexing measurements, are used with PTT values measured from the ECG and PPG waveforms to determine cNIBP (step 410). PPG waveforms measured with both red and infrared waveforms are additionally processed to determine SpO2, as described above, using modified calculation parameters tailored for the base of the thumb (step 411).

The body-worn monitor makes the above-described measurements for PTT-based cNIBP by collecting data for 20-second periods, and then processing these data with a variety of statistical averaging techniques as described above. Additionally, algorithms that process ECG and accelerometer waveforms using adaptive filtering can determine respiration rate, as described in the following patent application, the contents of which have been previously incorporated herein by reference: BODY-WORN MONITOR FOR MEASURING RESPIRATION RATE (U.S. Ser. No. 12/559,442; filed Sep. 14, 2009) (step 412). Heart rate and temperature are then determined as described in the following patent application, the contents of which have been already incorporated herein by reference: BODY-WORN VITAL SIGN MONITOR (U.S. Ser. No. 12/560,087; filed Sep. 15, 2009) (step 413).

All the vital signs described above are typically calculated with a technique for rolling averages that updates them every second. Every 4-8 hours the indexing measurement is repeated, either with a complete inflation-based measurement (step 402), or one based on partial inflation (step 403) as described above.

Other Embodiments

In addition to those methods described above, a number of additional methods can be used to calculate blood pressure from the PPG and ECG waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) VITAL SIGN MONITOR FOR ATHLETIC APPLICATIONS (U.S. Ser. No.; filed Sep. 13, 2004); 5) CUFFLESS BLOOD PRESSURE MONITOR AND ACCOMPANYING WIRELESS MOBILE DEVICE (U.S. Ser. No. 10/967,511; filed Oct. 18, 2004); 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306,243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser. No. 11/420,281; filed May 25, 2006); 15) SYSTEM FOR MEASURING VITAL SIGNS USING BILATERAL PULSE TRANSIT TIME (U.S. Ser. No. 11/420,652; filed May 26, 2006); 16) BLOOD PRESSURE MONITOR (U.S.S.N. 11/530,076; filed Sep. 8, 2006); 17) TWO-PART PATCH SENSOR FOR MONITORING VITAL SIGNS (U.S. Ser. No. 11/558,538; filed Nov. 10, 2006); and, 18) MONITOR FOR MEASURING VITAL SIGNS AND RENDERING VIDEO IMAGES (U.S. Ser. No. 11/682,177; filed Mar. 5, 2007).

Other embodiments are also within the scope of the invention. For example, other measurement techniques, such as conventional oscillometry measured during deflation, can be used to determine SYS for the above-described algorithms. Additionally, processing components and sensors for measuring SpO2 similar to those described above can be modified and worn on other portions of the patient's body. For example, sensors with finger-ring configurations can be worn on fingers other than the thumb. Or they can be modified to attach to other conventional sites for measuring SpO2, such as the ear, forehead, and bridge of the nose. In these embodiments the processing component can be worn in places other than the wrist, such as around the neck (and supported, e.g., by a lanyard) or on the patient's waist (supported, e.g., by a clip that attaches to the patient's belt). In still other embodiments the probe and processing component are integrated into a single unit.

In other embodiments, a set of body-worn monitors can continuously monitor a group of patients, wherein each patient in the group wears a body-worn monitor similar to those described herein. Additionally, each body-worn monitor can be augmented with a location sensor. The location sensor includes a wireless component and a location-processing component that receives a signal from the wireless component and processes it to determine a physical location of the patient. A processing component (similar to that described above) determines from the time-dependent waveforms at least one vital sign, one motion parameter, and an alarm parameter calculated from the combination of this information. A wireless transceiver transmits the vital sign, motion parameter, location of the patient, and alarm parameter through a wireless system. A remote computer system featuring a display and an interface to the wireless system receives the information and displays it on a user interface for each patient in the group.

In embodiments, the interface rendered on the display at the central nursing station features a field that displays a map corresponding to an area with multiple sections. Each section corresponds to the location of the patient and includes, e.g., the patient's vital signs, motion parameter, and alarm parameter. For example, the field can display a map corresponding to an area of a hospital (e.g. a hospital bay or emergency room), with each section corresponding to a specific bed, chair, or general location in the area. Typically the display renders graphical icons corresponding to the motion and alarm parameters for each patient in the group. In other embodiments, the body-worn monitor includes a graphical display that renders these parameters directly on the patient.

Typically the location sensor and the wireless transceiver operate on a common wireless system, e.g. a wireless system based on 802.11, 802.15.4, or cellular protocols. In this case a location is determined by processing the wireless signal with one or more algorithms known in the art. These include, for example, triangulating signals received from at least three different base stations, or simply estimating a location based on signal strength and proximity to a particular base station. In still other embodiments the location sensor includes a conventional global positioning system (GPS).

The body-worn monitor can include a first voice interface, and the remote computer can include a second voice interface that integrates with the first voice interface. The location sensor, wireless transceiver, and first and second voice interfaces can all operate on a common wireless system, such as one of the above-described systems based on 802.11 or cellular protocols. The remote computer, for example, can be a monitor that is essentially identical to the monitor worn by the patient, and can be carried or worn by a medical professional. In this case the monitor associated with the medical professional features a GUI wherein the user can select to display information (e.g. vital signs, location, and alarms) corresponding to a particular patient. This monitor can also include a voice interface so the medical professional can communicate directly with the patient.

In other embodiments, a variety of software configurations can be run on the body-worn monitor to give it a PDA-like functionality. These include, for example, Micro C OS®, Linux®, Microsoft Windows®, embOS, VxWorks, SymbianOS, QNX, OSE, BSD and its variants, FreeDOS, FreeRTOX, LynxOS, or eCOS and other embedded operating systems. The monitor can also run a software configuration that allows it to receive and send voice calls, text messages, or video streams received through the Internet or from the nation-wide wireless network it connects to. The barcode scanner described with reference to FIG. 25 can also be used to capture patient or medical professional identification information, or other such labeling. This information, for example, can be used to communicate with a patient in a hospital or at home. In other embodiments, the device can connect to an Internet-accessible website to download content, e.g., calibrations, software updates, text messages, and information describing medications, from an associated website. As described above, the device can connect to the website using both wired (e.g., CAN) or wireless (e.g., short or long-range wireless transceivers) means. In still other embodiments, 'alert' values corresponding to vital signs and the pager or cell phone number of a caregiver can be programmed into the device using its graphical user interface. If a patient's vital signs meet an alert criteria, software on the device can send a wireless 'page' to the caregiver, thereby alerting them to the patient's condition. For additional patient safety, a confirmation scheme can be implemented that alerts other individuals or systems until acknowledgment of the alert is received.

Still other embodiments are within the scope of the following claims.

What is claimed is:

1. A system for measuring a vital sign value from a patient, comprising:

(a) a first sensor configured to generate a first time-dependent signal indicative of one or more contractile properties of the patient's heart;

(b) a second sensor configured to generate a second time-dependent signal indicative of one or more contractile properties of the patient's heart, the second sensor comprising a radiation source configured to irradiate a portion of the patient, and a detector configured to detect radiation emitted from the radiation source after it passes through the portion of the patient, the detector comprising at least two pixel elements, each configured to generate a unique pixel element signal;

(c) a motion sensor configured to generate a motion signal indicative of movement of a region of the patient that the motion sensor is attached to; and, (d) a processing component configured to be worn on the patient's body, the processing component programmed to: (i) collectively analyze the pixel element signals generated by each of the at least two pixel elements and the motion signal; (ii) based on the collective analysis of the motion signal and the pixel element signals, select a pixel element signal from one of the at least two pixel elements characterized as having the lowest degree of motion corruption; and (iii) analyze the pixel element signal selected in (ii) to determine the vital sign value.

2. The system of claim 1, wherein the detector comprises at least a 3×3 array of pixels.

3. The system of claim 2, wherein each pixel in the array of pixels comprises a photodetector.

4. The system of claim 1, wherein the motion sensor is an accelerometer.

5. The system of claim 4, wherein the accelerometer is configured to generate a digital motion signal corresponding to each of the x, y, and z-axes.

6. The system of claim 1, wherein the processing component is programmed to analyze the motion signal and the pixel element signals to determine the pixel element signal that has the lowest correlation to the motion signal, wherein the pixel element having the lowest degree of motion corruption is identified by the pixel element signal having the lowest correlation to the motion signal as determined by a cross-correlation calculated between the motion signal and the pixel element signals.

7. The system of claim 1, wherein the processing component is programmed to analyze the motion signal to determine a measurement period when patient movement is relatively low, and then measure a signal from each pixel element.

8. The system of claim 1, wherein the first sensor comprises an ECG circuit and at least two electrodes.

9. The system of claim 8, wherein the first time-dependent signal comprises an ECG signal.

10. The system of claim 9, wherein the processing component is programmed to determine a QRS complex comprised by the ECG signal.

11. The system of claim 10, wherein the processing component is programmed to determine a time difference between the QRS complex and the onset point.

12. The system of claim 11, wherein the processing component is programmed to calculate a blood pressure value from the time difference.

13. The system of claim 8, wherein the first sensor is configured to be worn on the patient's chest.

14. The system of claim 1, wherein the signal selected from at least one of the pixel elements comprises a PPG signal.

15. The system of claim 14, wherein the processing component is programmed to determine an onset point in a portion comprised by the PPG signal.

16. The system of claim 1, further comprising a transceiver configured to be worn on the patient's arm that comprises the processing component.

17. The system of claim 16, wherein the transceiver comprises the motion sensor.

* * * * *